(12) United States Patent
Konduri et al.

(10) Patent No.: US 12,636,106 B1
(45) Date of Patent: May 26, 2026

(54) ARTICULATION ANGLE DETERMINATION FOR ENDOSCOPIC INSTRUMENTS

(71) Applicant: Auris Health, Inc., Santa Clara, CA (US)

(72) Inventors: Shyamprasad Konduri, Belmont, CA (US); Sean Fielding, San Mateo, CA (US); Chauncey F. Graetzel, Palo Alto, CA (US)

(73) Assignee: Auris Health, Inc., Santa Clara, CA (US)

( * ) Notice: Subject to any disclaimer, the term of this patent is extended or adjusted under 35 U.S.C. 154(b) by 287 days.

(21) Appl. No.: 18/583,745

(22) Filed: Feb. 21, 2024

Related U.S. Application Data

(60) Provisional application No. 63/486,223, filed on Feb. 21, 2023.

(51) Int. Cl.
*A61B 34/37* (2016.01)
*A61B 34/30* (2016.01)
A61B 34/10 (2016.01)
A61B 34/20 (2016.01)

(52) U.S. Cl.
CPC ........ *A61B 34/37* (2016.02); *A61B 2034/107* (2016.02); *A61B 2034/2059* (2016.02); *A61B 2034/301* (2016.02)

(58) Field of Classification Search
CPC ......... A61B 34/37; A61B 34/71; A61B 34/30;
A61B 2017/003; A61B 2017/00305;
A61B 2017/00309; A61B 2017/00314;
A61B 2017/00323; A61B 2017/00327;
A61B 2017/00331
See application file for complete search history.

(56) References Cited

U.S. PATENT DOCUMENTS

| | | | |
|---|---|---|---|
| 2017/0151027 A1* | 6/2017 | Walker | A61B 34/37 |
| 2019/0192144 A1* | 6/2019 | Parfett | A61B 17/07207 |
| 2023/0210604 A1* | 7/2023 | Berman | A61B 6/4441 |
| | | | 378/177 |

* cited by examiner

*Primary Examiner* — Sarah A Long
(74) *Attorney, Agent, or Firm* — Paradice & Li LLP

(57) ABSTRACT

The articulation angle is an important characteristic to quantify for open loop control and/or closed loop control of a medical instrument comprising an elongated body. The articulation angle may be computed using various techniques including using inverse trigonometric functions on vector representations of elongated body poses. The technique may involve projecting the vectors onto a measurement plane having a normal vector. The technique enable differentiation between positive and negative articulation directions. Additionally, the technique can enable the articulation angle to be computed even for high articulation angles, e.g., more than 180 degrees. The so computed articulation may be used for open loop or closed loop control of the elongated body.

20 Claims, 16 Drawing Sheets

Figure 2:
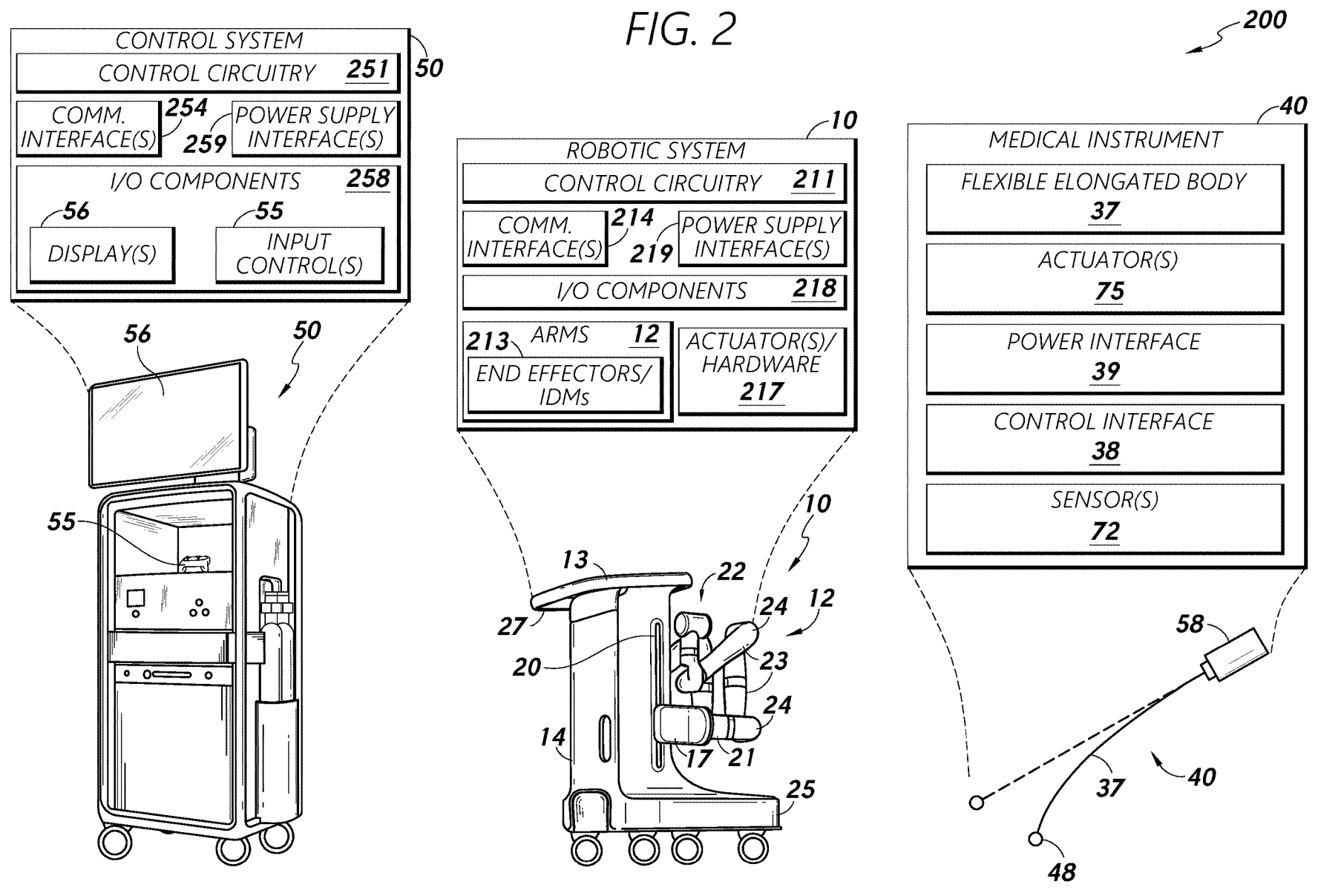

MEDICAL INSTRUMENT

FLEXIBLE ELONGATED BODY
37

ACTUATOR(S)
75

POWER INTERFACE
39

CONTROL INTERFACE
38

SENSOR(S)
72

58
40
37
48

10

ROBOTIC SYSTEM

CONTROL CIRCUITRY 211

COMM. INTERFACE(S) 214

POWER SUPPLY INTERFACE(S) 219

I/O COMPONENTS 218

ARMS 12

ACTUATOR(S)/ HARDWARE 217

END EFFECTORS/ IDMs 213

10
12
24
23
24
22
21
17
25
13
27
20
14

50

CONTROL SYSTEM

CONTROL CIRCUITRY 251

COMM. INTERFACE(S) 254

POWER SUPPLY INTERFACE(S) 259

I/O COMPONENTS 258

DISPLAY(S) 56

INPUT CONTROL(S) 55

50
56
55

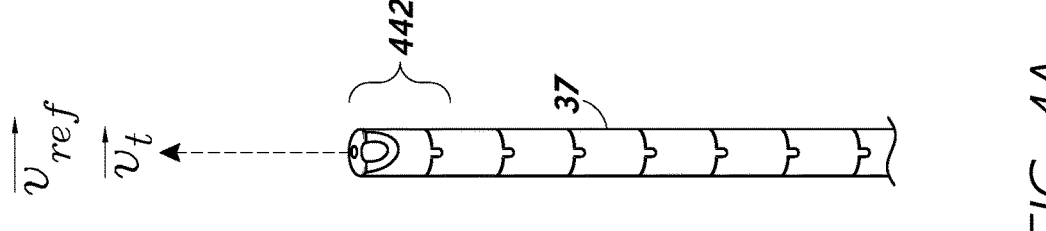
FIG. 4C
FIG. 4B
FIG. 4A

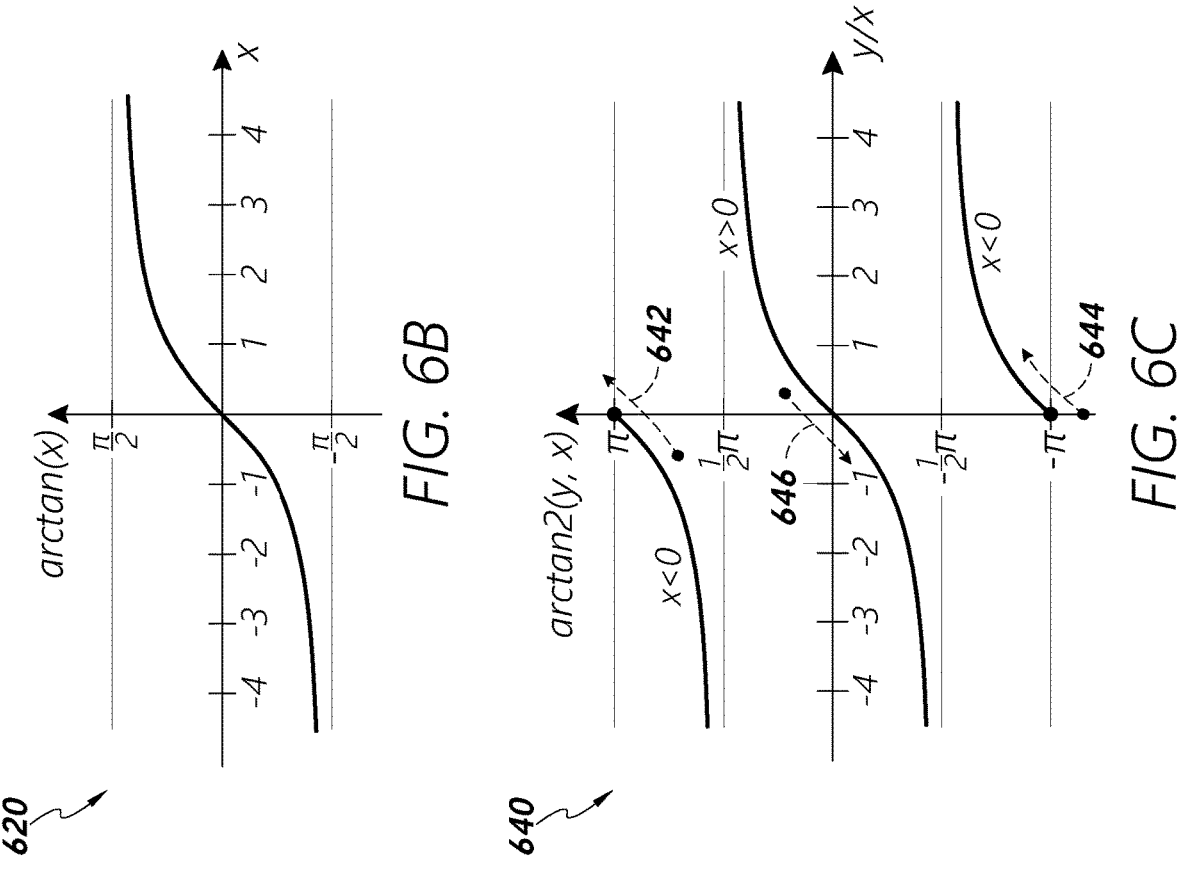
FIG. 6B
FIG. 6C
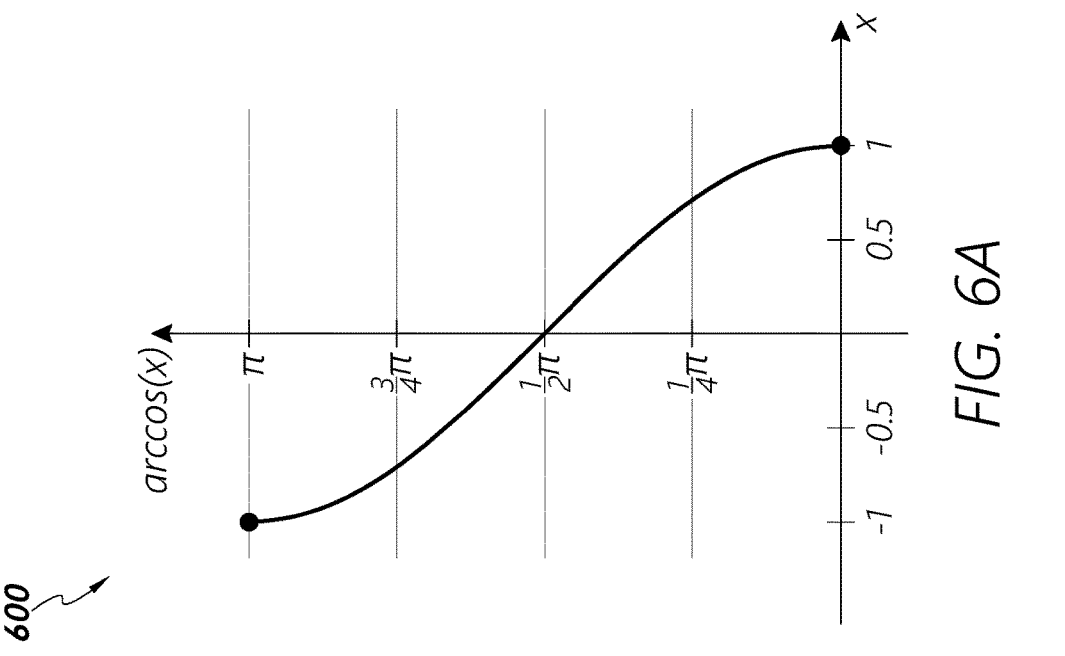
FIG. 6A

1100

1120

1140

1250

WHEN SECOND TARGET ANGLE IS REACHED: UPDATE MEASUREMENT PLANE; UPDATE NORMAL VECTOR; UPDATE COMPUTED ANGLE

1266

LOCK IN MEASUREMENT PLANE?

NO

YES

1276

END

1252

*1300*

ARTICULATION ANGLE DETERMINATION FOR ENDOSCOPIC INSTRUMENTS

RELATED APPLICATION(S)

This application claims priority to U.S. Provisional Application No. 63/486,223, filed Feb. 21, 2023, entitled CONTROLLING A MEDICAL INSTRUMENT FLEXIBLE ELONGATED BODY, the disclosure of which is hereby incorporated by reference in its entirety.

BACKGROUND

Field

The present disclosure relates to robotic medical systems and, particularly, to control of medical instruments that have flexible elongated bodies. In one aspect, the disclosure relates to characterizing articulation of such flexible elongated bodies. Other aspects are also disclosed.

Description of Related Art

Certain robotic medical procedures can involve the use of shaft-type instruments, such as endoscopes, which may be inserted into a patient through an orifice (e.g., a natural orifice) and advanced to a target anatomical site. Such medical instruments can be articulatable, such that the tip and/or other portion(s) of the shaft can deflect in one or more dimensions using robotic controls.

SUMMARY

Described herein are systems, devices, and methods to characterize a flexible elongated body of a medical instrument, such as a flexible endoscope, in which the present articulation of the elongated body is computed as an articulation angle. There are various angle computation methods but some of the methods are limited by the range of articulation angles that the method can compute. For example, an unsigned angle method may not be able to accurately compute for articulation angles that are large (e.g., more than 180 degrees). In contrast, a signed angle method can compute articulation angles accurately for such large articulation angles. The present disclosure describes various angle computation techniques and, for when the techniques may be lacking in one or more aspects, improve the techniques.

In some aspects, the techniques described herein relate to a method for controlling or characterizing a medical instrument, the method including: receiving at least one sensed pose of a distal end of a flexible elongated body; determining a reference vector; determining a pointing vector based on the at least one sensed pose; projecting the pointing vector onto a measurement plane; determining an articulation angle based on the projected pointing vector, the reference vector, and a normal vector associated with the measurement plane; and generating a command for controlling the flexible elongated body based on the articulation angle.

In some aspects, the techniques described herein relate to a method, further including: projecting the reference vector onto the measurement plane.

In some aspects, the techniques described herein relate to a method, wherein the determining the articulation angle includes: applying an inverse trigonometric function.

In some aspects, the techniques described herein relate to a method, wherein the inverse trigonometric function is an inverse tangent function.

In some aspects, the techniques described herein relate to a method, wherein the inverse tangent function has an output range of 360 degrees.

In some aspects, the techniques described herein relate to a method, wherein the normal vector represents a clockwise articulation or a counterclockwise articulation on the normal vector.

In some aspects, the techniques described herein relate to a method, wherein the determining the articulation angle includes: determining a cross product based on the reference vector and the pointing vector.

In some aspects, the techniques described herein relate to a method, wherein the determining the articulation angle includes: determining an inner product of the cross product and the normal vector.

In some aspects, the techniques described herein relate to a method, wherein the determining the articulation angle includes: determining that the articulation angle is negative; and based on the determination that the articulation angle is negative, adding 360 degrees to the articulation angle.

In some aspects, the techniques described herein relate to a method, wherein the determining the articulation angle includes: determining that a magnitude of the articulation angle is greater than a wraparound threshold; and based on the determination that a magnitude of the articulation angle is greater than a wraparound threshold, adding 360 degrees to the articulation angle.

In some aspects, the techniques described herein relate to a method, wherein the determining the articulation angle includes: determining that the articulation angle is negative; and based on the determination that the articulation angle is negative, reversing a direction of the normal vector.

In some aspects, the techniques described herein relate to a method, wherein the determining the articulation angle includes: determining that the articulation angle is negative; and based on the determination that the articulation angle is negative, changing a sign of the articulation angle to positive.

In some aspects, the techniques described herein relate to a method, wherein the pointing vector is of an initial articulation, the method further including: determining that the articulation angle is negative; and based on the determination that the articulation angle is negative: changing a sign of the articulation angle to positive; and reversing a direction of the normal vector.

In some aspects, the techniques described herein relate to a method, further including: accumulating articulation history of the flexible elongated body, wherein the articulation history includes a time sequence of one or more pointing vectors; determining a plane of best fit for the articulation history; and updating the measurement plane with the plane of best fit.

In some aspects, the techniques described herein relate to a method, wherein the updating the measurement plane is in response to a determination that the articulation angle has reached a target angle.

In some aspects, the techniques described herein relate to a method, wherein the updating the measurement plane includes: applying a transformation matrix to the measurement plane.

In some aspects, the techniques described herein relate to a method, further including: determining that an amount of the articulation history is greater than a threshold amount; and based on the determination that the amount of the articulation history is greater than the threshold amount, preventing the measurement plane from further updates.

In some aspects, the techniques described herein relate to a method, wherein the determining the articulation angle includes: determining that the articulation angle is less than a threshold; and based on the determination that the articulation angle is less than the threshold, determining an articulation angle based on the pointing vector and the reference vector using inverse cosine function.

In some aspects, the techniques described herein relate to a system, including: control circuitry configured to communicatively couple to a flexible elongated body of a medical instrument; wherein the control circuitry is configured to: receive at least one sensed pose of a distal end of the flexible elongated body; determine a reference vector; determine a pointing vector based on the at least one sensed pose; project the pointing vector onto a measurement plane; determine an articulation angle based on the projected pointing vector, the reference vector, and a normal vector associated with the measurement plane; and generate a command for controlling the flexible elongated body based on the articulation angle.

In some aspects, the techniques described herein relate to a non-transient computer readable medium containing program instructions for causing a computer to perform a method of: receiving at least one sensed pose of a distal end of a flexible elongated body of a medical instrument; determining a reference vector; determining a pointing vector based on the at least one sensed pose; projecting the pointing vector onto a measurement plane; determining an articulation angle based on the projected pointing vector, the reference vector, and a normal vector associated with the measurement plane; and generating a command for controlling the flexible elongated body based on the articulation angle.

For purposes of summarizing the disclosure, certain aspects, advantages and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

FIG. 2 illustrates a schematic view of different components of the medical system of FIG. 1, in accordance with one or more embodiments.

FIGS. 4A-4C illustrate a flexible elongated body of a medical instrument, in three different example states of articulation or bending, namely unarticulated or 0 degrees, 90 degrees, and 270 degrees, in accordance with one or more embodiments.

FIGS. 6A-6C illustrate various inverse trigonometric curves, in accordance with one or more embodiments.

DETAILED DESCRIPTION

Figure 1:
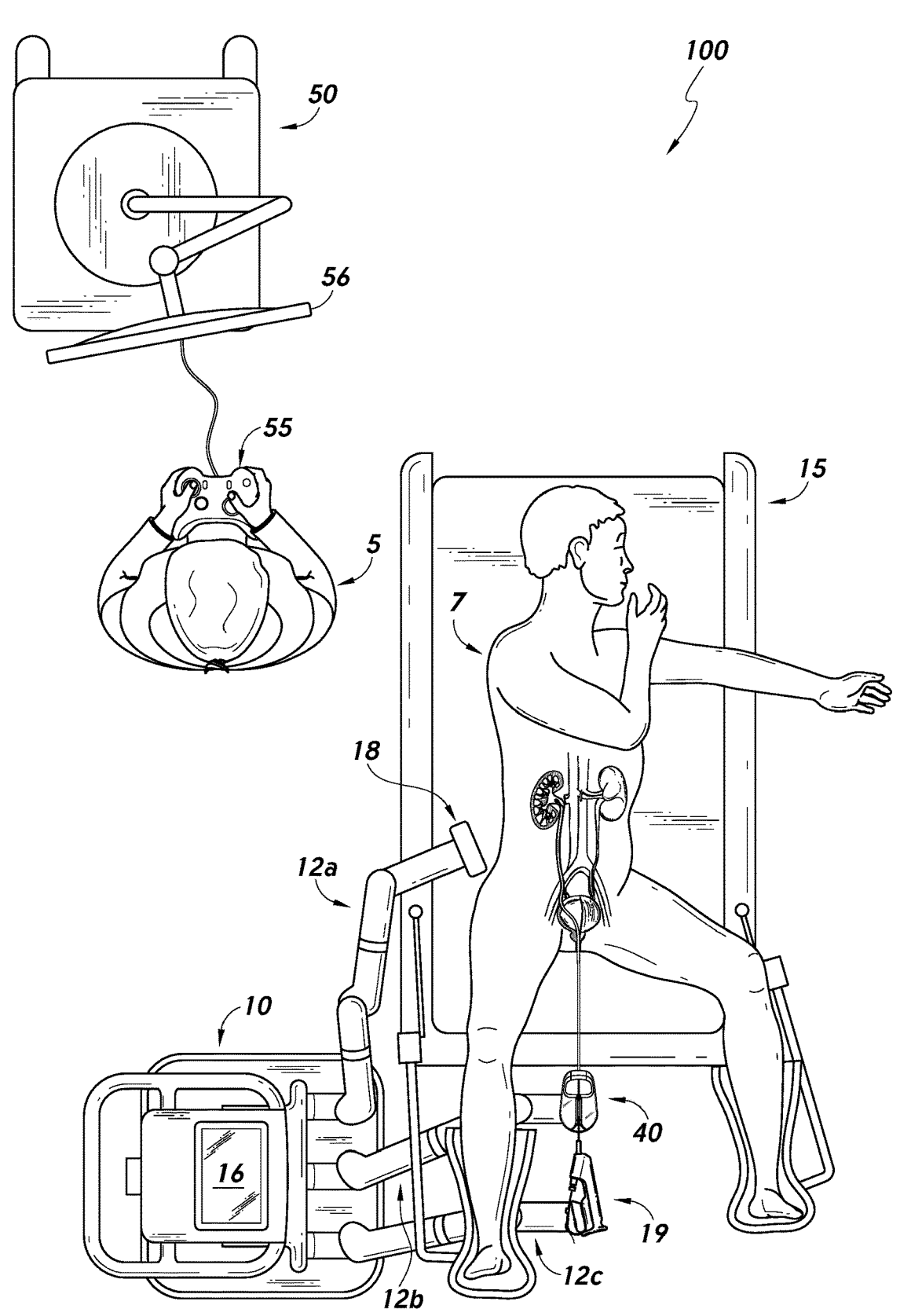
FIG. 1 illustrates an example medical system that may be used for performing various procedures, in accordance with one or more embodiments.

The headings provided herein are for convenience only and do not necessarily affect the scope or meaning of the claimed invention. Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Although certain spatially relative terms, such as "outer," "inner," "upper," "lower," "below," "above," "vertical,"

"horizontal," "top," "bottom," "lateral," "upwardly," "side," and similar terms, are used herein to describe a spatial relationship of one device/element or anatomical structure to another device/element or anatomical structure, it is understood that these terms are used herein for ease of description to describe the positional relationship between element(s)/structures(s), such as with respect to the illustrated orientations of the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of a subject or element/structure, and vice-versa. It should be understood that spatially relative terms, including those listed above, may be understood relative to a respective illustrated orientation of a referenced figure.

Certain reference numbers are re-used across different figures of the figure set of the present disclosure as a matter of convenience for devices, components, systems, features, and/or modules having features that may be similar in one or more respects. However, with respect to any of the embodiments disclosed herein, re-use of common reference numbers in the drawings does not necessarily indicate that such features, devices, components, or modules are identical or similar. Rather, one having ordinary skill in the art may be informed by context with respect to the degree to which usage of common reference numbers can imply similarity between referenced subject matter. Use of a particular reference number in the context of the description of a particular figure can be understood to relate to the identified device, component, aspect, feature, module, or system in that particular figure, and not necessarily to any devices, components, aspects, features, modules, or systems identified by the same reference number in another figure. Furthermore, aspects of separate figures identified with common reference numbers can be interpreted to share characteristics or to be entirely independent of one another. In some contexts, features associated with separate figures that are identified by common reference numbers are not related and/or similar with respect to at least certain aspects.

The present disclosure provides systems, devices, and methods for characterizing and controlling articulation of an instrument shaft, such as a medical endoscope. Medical endoscopes are generally flexible and compliant, thus typically include mechanisms that can be bent or articulated to angles corresponding to high articulations (e.g., large articulation angles). Articulation of the endoscopes may be controlled with open loop control or closed loop control. Open loop control involves control action that is dependent on kinematic model but not actual output or feedback. In contrast, closed loop control involves control action that is dependent on the actual output or feedback. When it comes to endoscope articulation, the behavior of the endoscope can vary depending on the degree of bending, making it challenging to develop open loop controls to robotically control the endoscope across a full range of articulations. Closed loop controls may use articulation measurements as feedback to determine the appropriate control command when there is a discrepancy between expected and actual articulations. Accuracy of the articulation measurement may be important when used as feedback in a closed loop control system.

Articulation angle may be used to represent a degree of articulation of the endoscope. Articulation angles may be used in closed loop control of endoscopes as well as mechanical characterization and other control designs. An articulation angle of an endoscope may be computed or otherwise determined based on endoscope pose (e.g., position and/or orientation). In some embodiments, one or more sensors associated with the endoscope can provide the pose. For instance, an electromagnetic sensor mounted on a tip (e.g., a distal end) of the endoscope can provide the tip pose within an electromagnetic field applied to the sensor. The tip pose with respect to a reference pose can be used to compute the articulation angle.

The present disclosure observes that, as the flexible elongated body of an endoscope articulates away from an initial/reference pose toward a target pose, computing the correct articulation angle becomes more challenging. As mentioned, the flexible elongated body may be articulated to large articulation angles greater than 180 degrees. When at such large articulation angles, conventional articulation angle computation technique may fail to provide accurate measurements. The present disclosure describes various issues with the conventional articulation angle computation techniques and, additionally, addresses the issues with improved articulation angle computation techniques.

Medical System

Various aspects of the present disclosure described herein may be integrated into a robotically enabled/assisted medical system, including a surgical robotic system (robotic system for short), capable of performing a variety of medical procedures, including both minimally invasive, such as laparoscopy, and non-invasive, such as endoscopy, procedures. Among endoscopy procedures, the robotically enabled medical system may be capable of performing bronchoscopy, ureteroscopy, gastroscopy, etc.

In addition to performing the breadth of procedures, the robotically enabled medical system may provide additional benefits, such as enhanced imaging and guidance to assist the medical professional. Additionally, the robotically enabled medical system may provide the medical professional with the ability to perform the procedure from an ergonomic position without the need for awkward arm motions and positions. Still further, the robotically enabled medical system may provide the medical professional with the ability to perform the procedure with improved ease of use such that one or more of the instruments of the robotically enabled medical system may be controlled by a single operator.

FIG. 1 shows an example medical system 100 that may be used for performing various procedures in accordance with aspects of the present disclosure. The medical system 100 may be used for, for example, endoscopic (e.g., ureteroscopic) procedures. The principles disclosed herein may be implemented in any type of endoscopic (e.g., bronchial, gastrointestinal, etc.) and/or percutaneous procedure.

The medical system 100 includes a robotic system 10 (e.g., a mobile robotic cart) that is configured to engage with and/or control one or more medical instruments 40 (e.g., a surgical tool or instrument such as a scope, a basketing system, etc.) via one or more robotic arms 12 to perform a direct-entry procedure on a subject 7 (e.g., a patient, a test subject, a simulation model, etc.). The term "subject" is used herein to refer to live patient as well as any subjects to which the present disclosure may be applicable. For example, the "subject" may refer to subjects including physical anatomic models (e.g., anatomical education model, anatomical model, medical education anatomy model, etc.) used in dry runs, models in computer simulations, or the like that covers non-live patients or subjects. The robotic system 10 is given commands by a control system 50 which is responsive to manual input from an operator 5. In some versions, the control system 50 is configured to receive images and/or image data from the medical instrument 40 (e.g., a scope) representing internal anatomy of the subject 7 and can display images based thereon.

It should be understood that the direct-entry instruments operated through the systems 10, 50 may include any type of medical instrument or combination of instruments, including an endoscope (such as a ureteroscope), catheter (such as a steerable or non-steerable catheter), nephroscopes, laparoscope, basketing systems, and/or other types of medical instruments. The medical instruments disclosed herein may be configured to navigate within the human anatomy, such as within a natural orifice or lumen of the human anatomy.

The medical instrument 40 has a flexible elongated body that has mechanical couplings which enable the elongated body to flex, bend, deflect or articulate to some angle, in response to an actuator (e.g., containing a motor) being energized in accordance with a command (also referred to as an input, which refers to (e.g., defines) a desired direction or a desired articulation angle, for example). An example of such a medical instrument is a flexible endoscope (or scope) that may be any type of elongated medical instrument having image generating, viewing, and/or capturing functionality and configured to be introduced into any type of organ, cavity, lumen, chamber, or space of a patient's body. A scope may include, for example, a ureteroscope (e.g., for accessing the urinary tract), a laparoscope, a nephroscope (e.g., for accessing the kidneys), a bronchoscope (e.g., for accessing an airway, such as the bronchus), a colonoscope (e.g., for accessing the colon), an arthroscope (e.g., for accessing a joint), a cystoscope (e.g., for accessing the bladder), colonoscope (e.g., for accessing the colon and/or rectum), borescope, and so on. The elongated body may comprise a flexible tube or shaft and may be dimensioned to be passed within an outer sheath, catheter, introducer, or other lumen-type device, or it may be used without such devices.

The medical system 100 shown as an example in the figures further includes a table 15, and an electromagnetic (EM) field generator 18. Table 15 is configured to hold the subject 7 for example as shown. EM field generator 18 may be held by one of the robotic arms (robotic arm 12a) of the robotic system 10 or it may be a stand-alone device. In some versions, the table has actuators which can change, for example the height and orientation of the table 15. The control system 50 may communicate with the table 15 to position the table 15 in a particular orientation or otherwise control the table 15.

As shown in FIG. 1 and FIG. 2, the control system 50 of the present example includes various input/output (I/O) components 258 configured to assist the operator 5 or others in performing a medical procedure. For example, the I/O components 258 may be configured to allow for user input to control/navigate the medical instrument 40) within the subject 7. I/O components 258 of the present example include a controller 55 that is configured to receive user input from the operator 5; and a display 56 that is configured to present certain information to assist the operator. Controller 55 may take any suitable form, including but not limited to one or more buttons, keys, joysticks, handheld controllers (e.g., video-game-type controllers), computer mice, trackpads, trackballs, control pads, and/or sensors (e.g., motion sensors or cameras) that capture hand gestures and finger gestures, touchscreens, etc.

As also shown in FIG. 2, control system 50 of the present example includes a communication interface 254 that is operable to provide a communicative interface between control system 50 and robotic system 10, medical instrument 40, and/or other components. Communications via communication interface 254 may include data, commands, electrical power, and/or other forms of communication. Communication interface 254 may also be configured to provide communication via wire, wirelessly, and/or other modalities. Control system 50 also includes a power supply interface 259, which may receive power to drive control system 50 via wire, battery, and/or any other suitable kind of power source. A control circuitry 251 of the control system 50 may provide signal processing and execute control algorithms to achieve the functionality of the medical system 100 as described herein.

The control system 50 may also communicate with the robotic system 10 to receive pose data therefrom relating to the pose (e.g., position and/or orientation) of the distal end of the medical instrument flexible elongated body 37. Such pose data may be derived using one or more electromagnetic sensors that may be mounted to the flexible elongated body 37 of the medical instrument 40, and that interact with an EM filed generated by the EM field generator 18. The control system 50 may communicate with the EM field generator 18 to control the generation of the EM field in an area around the subject 7. Other ways of detecting the pose (e.g., 3D position and/or orientation) of the distal end of the medical instrument 40 are possible, such as using an optical camera/imaging-based system.

As noted above and as shown in FIG. 1 and FIG. 2, the robotic system 10 includes robotic arms 12 that are configured to engage with and/or control the medical instrument 40 to perform one or more aspects of a procedure. It should be understood that a robotic arm 12 may be coupled to instruments that are different than those shown in FIG. 1; and in some scenarios, one or more of the robotic arms 12 may not be utilized or coupled to a medical instrument. Each robotic arm 12 includes multiple arm segments 23 coupled to joints 24, which enable the attached medical instrument to have multiple degrees of movement/freedom. In the example of FIG. 1, the robotic system 10 is positioned proximate to the patient's legs and the robotic arms 12 are actuated to engage with and position the medical instrument 40 for access into an access opening of the subject 7. When the robotic system 10 is properly positioned, the medical instrument 40 may be inserted into the subject 7 robotically using the robotic arms 12, manually by the operator 5, or a combination thereof.

In the case of the medical instrument 40 being a scope, a scope-driver instrument coupling 11, or more generally an instrument device manipulator (IDM), may be attached to the distal end of one of the arms (robotic arm 12b) to facilitate robotic control/advancement of the scope, while an instrument coupling/manipulator 19 that is attached to another of the arms (robotic arm 12c) is configured to facilitate advancement and operation of a basketing device (not shown). The medical instrument 40 may include one or more working channels through which additional tools, such as lithotripters, basketing devices, forceps, etc., may be introduced into the treatment site.

The robotic system 10 may be coupled to any component of the medical system 100, such as the control system 50, the table 15, the EM field generator 18, the medical instrument 40, and/or any type of percutaneous-access instrument (e.g., needle, catheter, nephroscope, etc.). As noted above, robotic system 10 may be communicatively coupled with control system 50 via communication interfaces 214, 254. Robotic system 10 also includes a power supply interface 219, which may receive power to drive robotic system 10 via wire, battery, and/or any other suitable kind of power source. In addition, robotic system 10 one example includes various input/output (I/O) components 218 configured to assist the operator 5 or others in performing a medical procedure. Such I/O components 218 may include any of the various kinds of I/O components 258 described herein in the context of the control system 50. In addition, or in the alternative, I/O components 218 of robotic system 10 may take any suitable form (or may be omitted altogether).

Robotic system 10 of the present example generally includes a column 14, a base 25, and a console 13 at the top of the column 14. I/O components 218 may be positioned at the upper end of column 14. Console 13 also includes a handle 27 to assist with maneuvering and stabilizing the robotic system 10. The column 14 may include one or more arm supports 17 (also referred to as a "carriage") for supporting the deployment of the one or more robotic arms 12 (where three robotic arms 12a, 12b, 12c are shown in FIG. 1). The arm support 17 may include individually configurable arm mounts that rotate about a perpendicular axis to adjust the base of the robotic arms 12 for desired positioning relative to the patient. In some versions, the arm support 17 may be connected to the column 14 through slots 20 that are positioned on opposite sides of the column 14 to guide vertical translation of the arm support 17 along column 14. The robotic arms 12 of the present example generally comprise robotic arm bases 21 and end effectors 22, separated by a series of linking arm segments 23 that are connected by a series of joints 24, each joint comprising one or more independent actuators 217. Each actuator 217 may comprise an independently controllable motor.

The end effector of each of the robotic arms 12 may include an instrument device manipulator (IDM 213), which may be attached using a mechanism changer interface (MCI). The MCI may provide power and control interfaces (e.g., connectors to transfer pneumatic pressure, electrical power, electrical signals, and/or optical signals from the robotic arm 12) to the IDM 213. In some versions, the IDM 213 may be removed and replaced with a different type of IDM 213, depending on the type of the medical instrument 40 that is to be attached to the arm. Each type of IDM 213 may serve to manipulate a respective type of the medical instrument 40. In the case where the medical instrument is a scope, the IDM 213 may use any one or combination of techniques including, for example, direct drives, harmonic drives, geared drives, belts and pulleys, magnetic drives, and the like, to drive the flexible elongated body of the scope so that the distal end is positioned to some desired angle or bent in some desired direction. A second type of IDM 213 may manipulate a basketing system or a steerable catheter by driving the flexible elongated body of the catheter or basketing system so that the distal end is positioned at some angle. Another type of IDM 213 may be configured to hold the EM field generator 18.

The medical system 100 may include certain control circuitry configured to perform certain of the functionality described herein, including the control circuitry 211 of the robotic system 10 and the control circuitry 251 of the control system 50. That is, the control circuitry of the medical system 100 may be part of the robotic system 10, the control system 50, or some combination thereof. The term "control circuitry" is used herein according to its broad and ordinary meaning, and may refer to any collection of processors, processing circuitry, processing modules/units, chips, dies (e.g., semiconductor dies including come or more active and/or passive devices and/or connectivity circuitry), microprocessors, micro-controllers, digital signal processors, microcomputers, central processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry referenced herein may further include one or more circuit substrates (e.g., printed circuit boards), conductive traces and vias, and/or mounting pads, connectors, and/or components. Control circuitry referenced herein may further comprise one or more storage devices, which may be embodied in a single memory device, a plurality of memory devices, and/or embedded circuitry of a device. Such data storage may comprise read-only memory, random access memory, volatile memory, non-volatile memory, static memory, dynamic memory, flash memory, cache memory, data storage registers, and/or any device that stores digital information. It should be noted that in versions in which control circuitry comprises a hardware and/or software state machine, analog circuitry, digital circuitry, and/or logic circuitry, data storage device(s)/register(s) storing any associated operational instructions may be embedded within, or external to, the circuitry comprising the state machine, analog circuitry, digital circuitry, and/or logic circuitry.

The control circuitry 211, 251 may comprise computer-readable media storing, and/or configured to store, hard-coded and/or operational instructions corresponding to at least some of the steps and/or functions illustrated in one or more of the present figures and/or described herein. Such computer-readable media may be included in an article of manufacture in some instances. The control circuitry 211, 251 may be entirely locally maintained/disposed or may be remotely located at least in part (e.g., communicatively coupled indirectly via a local area network and/or a wide area network).

In some versions, for example, the operator 5 may provide input to the control system 50 and/or robotic system 10; and in response to such input, control signals may be sent to the robotic system 10 to manipulate the medical instrument 40. The control system 50 may include one or more display devices (display 56) to provide various information regarding a procedure. For example, the display 56 may provide information regarding the medical instrument 40. In the case of a scope, the control system 50 may receive real-time images that are captured by the scope and display the real-time images via the display 56.

As shown in FIG. 2, there may be an imaging device 48 at the distal end of the flexible elongated body 37 which may be powered through a power interface 39 and/or controlled through a control interface 38, each or both of which may interface with a robotic arm/component of the robotic system 10. The medical instrument 40 may have one or more other sensors (sensor 72), such as pressure and/or other force-reading sensors, which may be configured to generate signals indicating forces experienced at or by one or more actuators (actuator 75) and/or other couplings of the medical instrument 40.

Medical Instrument

Figure 3:
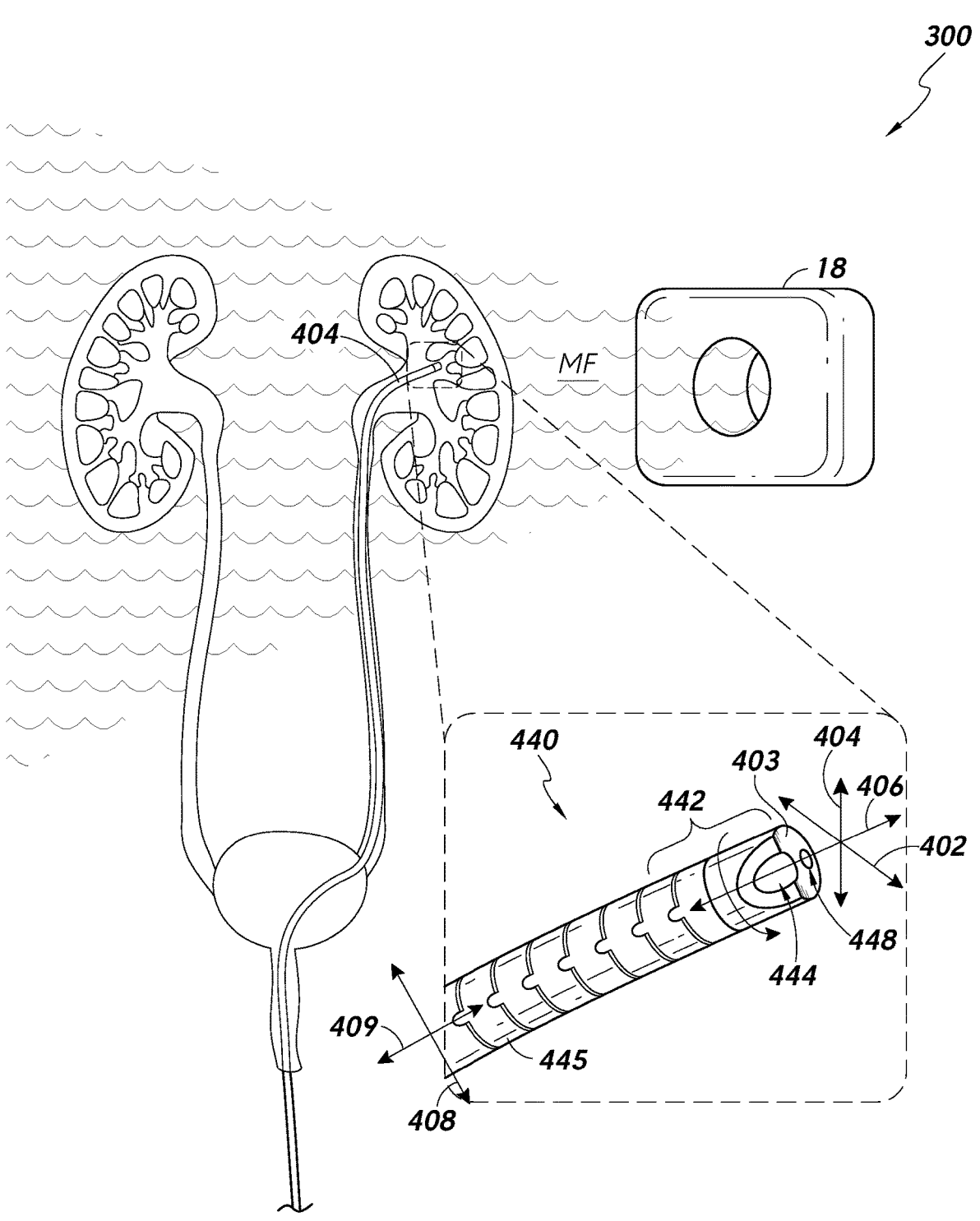
FIG. 3 illustrates enlarged views of other components of the medical system of FIG. 1, including a distal end of an example medical instrument, in accordance with one or more embodiments.

FIG. 3 shows an example of the medical instrument 40 described above, as a scope 440. Scope 440 of this example includes a working channel 444 that may be formed inside a flexible elongated body 37 which is a flexible elongated body. The working channel 444 may serve for deploying therein a component of the medical instrument, e.g., a lithotripter, a basketing system, forceps, or for performing irrigation and/or aspiration, out through a distal end 442 of the scope 440, into an operative region surrounding the distal end 442. The scope 440 and in particular the flexible elongated body 37 may be articulated, such as with respect to at least the distal end 442, so that the scope 440 and in particular its distal end can be steered within the human anatomy. In some versions, the scope 440 is configured to be articulated with, for example, five degrees of freedom, including XYZ coordinate movement, as well as pitch and yaw. In some versions, the scope 440 has six degrees of freedom, including X, Y, and Z positions, as well as pitch, tilt or roll, and yaw. Position sensors of the scope 440 may likewise have similar degrees of freedom with respect to the position information they produce or provide. As shown in FIG. 3, the deflection of the flexible elongated body 37 may be defined by the resulting angle that is formed between the distal end 442 and a longitudinal axis 406 of the flexible elongated body 37 when the latter is in an unbent state as shown. The longitudinal axis 406 is also referred to below as a "roll axis" of the scope 440.

In the present example, the scope 440 can accommodate wires and/or optical fibers to transfer signals to/from an optical assembly at the distal end 442. The optical assembly may include an imaging device 448 such as an optical camera. The imaging device 448 may be used to capture images of an internal anatomical space of the subject 7. The scope 440 may further be configured to accommodate optical fibers to carry light from proximately located light sources, such as light-emitting diodes, to the distal end 442. The distal end 442 may include ports for light sources to illuminate an anatomical space when using the imaging device 448. The imaging device 448 may comprise one or more optical components as needed to illuminate the field of view of the imaging device, e.g., an optical fiber, a fiber array, a lens, a light-emitting diode, etc. all of which may be housed at the distal end 442. The optical components of the imaging device 448 move along with, or as one with, the distal end 442, such that movement of the distal end 442 results in changes to the images that are being captured simultaneously by the imaging device 448.

To capture images at different orientations of the distal end 442, robotic system 10 may be configured to deflect the distal end 442 on a yaw axis 402, a pitch axis 404, or a roll axis that coincides with the longitudinal axis 406. This may be enabled by the flexible elongated body 37 which is an elongated body that could be elongated or translated in the longitudinal axis 406, an x-axis 408, or a y-axis 409. The scope 440 may include a reference structure (not shown) to calibrate the position of the scope 440. For example, the robotic system 10 and/or control system 50 may measure deflection or bending of the flexible elongated body 37 of the scope 440 relative to the reference structure. The reference structure may be located, for example, on a proximal end of the scope 440 and may include a key, slot, or flange.

In one instance, one of the robotic arms (e.g., robotic arm 12b) of the robotic system 10 may be configured/configurable to manipulate the scope 440 as described above. A scope-driver instrument coupling 11, or more broadly an instrument device manipulator (IDM), may be attached to the distal end of the robotic arm 12b. The IDM, and in this case the scope-driver instrument coupling 11, contains an actuator that becomes mechanically coupled to a transmission in the scope 440, when the scope 440 has been attached to the IDM, to facilitate robotic control/advancement of the bending of the scope 440. Such manipulation may be performed by energizing the actuator which actuates one or more of the elongated transmission elements in the scope 440, such as one or more pull wires (e.g., pull or push wires), cables, fibers, and/or flexible shafts. For example, the robotic arm 12 may be configured with to actuate multiple pull wires (not shown) coupled to the scope 440, which results in deflecting the distal end 442 to some desired angle or in some desired direction. Pull wires may include any suitable or desirable materials that have limited stretching characteristics, such as metallic and non-metallic materials such as stainless steel, Kevlar, tungsten, carbon fiber, and the like. In some versions, the scope 440 is configured to exhibit nonlinear behavior in response to the forces applied by the elongated transmission elements. The nonlinear behavior may be based on stiffness and compressibility of the scope 440, as well as variability in slack or stiffness between different members that make up the flexible elongated body 37.

In another version of the medical instrument 40, still referring to FIG. 2, the actuator 75 which actuates the elongated transmission elements of the scope 440 (to result in bending of the flexible elongated body 37) is contained within a housing of the scope 440. In this version, the command which is generated by the robotic system 10 to bend the flexible elongated body 37 may be translated into an actuator control signal that is signaled through the control interface 38, while the actuator 75 is powered through the power interface 39.

In some versions, the scope 440 includes at least one sensor 403 that is configured to generate and/or send sensor position data to another device. The sensor position data can indicate a position and/or orientation of the scope 440, e.g., the distal end 442 thereof, and/or may be used to determine or infer a position/orientation of the scope 440. For example, the sensor 403 (sometimes referred to as a "position sensor") may include an electromagnetic (EM) sensor with a coil of conductive material or other form of an antenna that produces an output signal in the presence of an EM field (such as one produced by the EM field generator 18). In some versions, the position sensor is positioned on the distal end 442, while in other embodiments the sensor 403 is positioned at another location on the scope 440. As shown in the example of FIG. 3, EM field generator 18 is configured to broadcast a magnetic field (denoted "MF") that is detected by the sensor 403 being in this case an EM position sensor. The magnetic field induces small currents in coils of the EM position sensor, which may be analyzed by a digital processor to determine a distance and/or angle/orientation between the EM position sensor and the EM field generator 18, which is then interpreted by the processor to determine the 3D position of the distal end 442 and optionally the orientation of the imaging device 448. It should be understood that the sensor 403 and the associated 3D position tracking subsystem may be of another type, such as an optical marker as part of an optical 3D tracking subsystem, a shape sensing fiber, an accelerometer, a gyroscope, a satellite-based positioning sensor (e.g., a global positioning system (GPS) sensor), a radio-frequency transceiver, and so on. In the present example, the EM position sensor of scope 440 provides sensor data to control system 50, which is then used to determine a position and/or an orientation of the scope 440. Controlling the Medical Instrument Flexible Elongated Body Turning now to FIGS. 4-6, these figures illustrate various aspects of controlling or characterizing the flexible elongated body 37 of the medical instrument 40. Articulation angles of the flexible elongated body 37 computed can be used in open loop or closed loop control of the medical instrument 40, to position or orient the distal end 442 of the flexible elongated body 37 as desired, as part of the medical system 100 described above in connection with FIGS. 1-2.

FIGS. 4A-4C illustrates the flexible elongated body 37 having been bent into three different example articulation angles, directions, or states of articulation or bending. While a skilled person would recognize that alternate representations of the articulation angles are also possible, the skilled person would appreciate that the articulation angles can be readily represented as angles between vectors. Specifically, a reference pose can be represented with a reference vector, $v_{ref}$, common to articulation angles and a current pose of the distal end 442 of the flexible elongated body 37 can be represented with a pointing vector (e.g., a target vector, a pointing direction vector, a pose vector, a distal end vector, etc.), $v_t$, that points outward from and along the distal end 442. The reference vector may have been previously determined and stored or may represent a previously determined and stored pose of the distal end 442 (e.g., calibrated), or it may represent or be determined based on a sensed initial pose of the distal end 442 (e.g., upon initializing the medical instrument 40 for operation or as part of an in-the-field calibration process for the medical instrument 40). The pointing vector of the distal end 442 may be sensed using any suitable pose tracking subsystem (e.g., a 3D pose tracking subsystem) such as the EM field generator 18 and the sensor 403 configured as an EM sensor described above.

Referring back to FIGS. 4A-4C, the example articulation angles are measured angles from the reference vector to the pointing vector. Accordingly, the example articulation angles show an unarticulated or zero (0) degree articulation 410, ninety (90) degrees clockwise articulation 420, and two hundred seventy (270) degrees clockwise articulation 430. The present disclosure proposes various techniques of estimating or determining such articulation angles which, as will be described in detail below, is not a simple task.

Unsigned Angle Computation

For small articulation angles, or more generally, articulation angles of less than or equal to 180 degrees, the articulation angle of the flexible elongated body 37 can be computed as an unsigned angle, $\theta_{unsigned}$, using the following relationship:

$$\theta_{unsigned} = \cos^{-1}\left(\frac{v_{ref} \cdot v_t}{\|v_{ref}\| \|v_t\|}\right) \qquad \text{Equation (1)}$$

where $v_{ref}$ is the reference vector and the $v_t$ is the pointing vector. The unsigned angle method of Equation (1) computes the angle between two vectors. It can accurately estimate an angle between the reference vector and the pointing vector when the angle is in the range of 0 to 180 degrees (e.g., between 0 and $\pi$ in radians). For example, the 90 degrees clockwise articulation 420 in FIG. 4B may be accurately determined by Equation (1). However, there are two limitations to Equation (1) that makes it challenging to use the unsigned angle method for all articulation angles.

The first limitation is that Equation (1) cannot, on its own, distinguish between a clockwise articulation and a counterclockwise articulation due to the cosine function being an even function (i.e., cos (−θ)=cos (θ)). For instance, Equation (1) results in the same 90 degrees angle for both clockwise 90 degrees articulation 420 of FIG. 4B and counterclockwise 90 degrees articulation (e.g., $\theta_1$ of FIG. 9).

The second limitation is that Equation (1) cannot compute, result in, or otherwise provide an angle greater than 180 degrees. As an inverse cosine curve 600 of FIG. 6A shows, inverse cosine function of Equation (1) is defined for output range of angles within 0 to 180 degrees for any input domain. That is, while Equation (1) can accurately determine articulation angles smaller than 180 degrees, Equation (1) will inaccurately estimate, for articulation angles that are greater than 180 degrees, an articulation angle less than 180 degrees. As an example, the unsigned angle method of Equation (1) would estimate, for the 270 degrees articulation 430 of FIG. 4C, 90 degrees articulation angle. Combined with the first limitation, it is shown that the unsigned angle method of Equation (1) estimates the same articulation angle for and cannot differentiate the counterclockwise 90 degrees articulation ($\theta_1$ of FIG. 9) and the clockwise 270 degrees articulation ($\theta_2$ of FIG. 9).

Accordingly, the unsigned angle method may require more than Equation (1) to accurately estimate an articulation angle. As examples that may supplement Equation (1) such that the unsigned angle method may accurately determine articulation angles of full range, past observed pointing vectors (e.g., $v_{t-N}$, $v_{t-3}$, $v_{t-2}$, $v_{t-1}$ of FIG. 5), EM data or robot data indicative of past or current articulations, or the like may be contemplated. However, supplementing such additional data and modifying the unsigned angle computation method for various corner cases using the supplemented data can be cumbersome.

Signed Angle Computation

A signed angle method of the present disclosure can address both limitations of the unsigned angle method. The signed angle method can address the first limitation of the unsigned method relating to distinguishing clockwise articulation from counterclockwise articulation, or vice versa, by determining a signed articulation angle. For example, the signed angle method can compute a +90 degrees articulation angle for a clockwise articulation and a −90 degrees articulation angle for a counterclockwise articulation (or vice versa depending on a reference frame used). Additionally, the signed angle method can address the second limitation relating to large angles by correctly identifying and handling angles that articulated past 180 degrees. For example, the signed angle method can compute −90 degrees for the counterclockwise 90 degrees articulation ($\theta_1$ of FIG. 9) and +270 for the clockwise 270 degrees articulation ($\theta_2$ of FIG. 9).

For all articulation angles, the articulation angle of the flexible elongated body 37 can be computed as a signed angle, $\theta_{signed}$, using the following relationship:

$$\theta_{signed} = \tan^{-1}\frac{(v_{ref} \times v_t) \cdot n}{v_{ref} \cdot v_t} \qquad \text{Equation (2)}$$

where $v_{ref}$ and $v_t$ are, respectively, the reference vector and the pointing vector as described above, and n is a normal vector of a chosen measurement plane. One or more of the vectors may be normalized as normal vectors. It is observed that the cross product multiplication between the reference vector and the pointing vector computes a positive angle or a negative angle based on the right hand rule. That is, a computed signed angle reflects relative pose of the pointing vector in relation to the reference vector, unlike the signed angle method of Equation (1).

Figure 5:
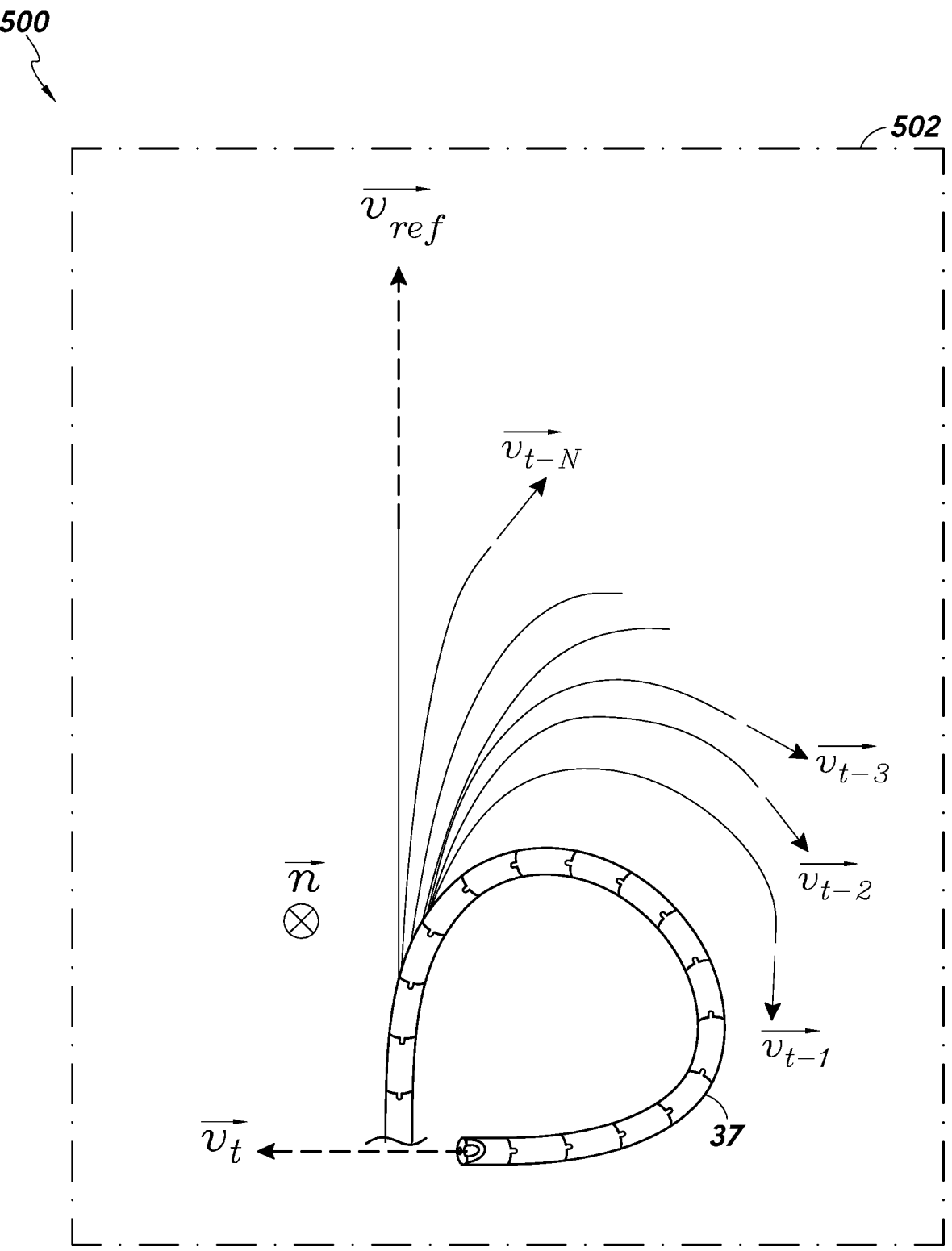
FIG. 5 illustrates an example large articulation that can be computed by the signed angle method, in accordance with one or more embodiments.

FIG. 5 illustrates an example large articulation 500 that can be computed by the signed angle method. The large articulation 500 from the reference vector to the pointing vector is on a plane of the drawing page (or the surface of the monitor) as indicated by a boundary 502. Assuming the plane is also the measurement plane, there may be two normal vectors, a first normal vector straight into the plane (the depicted normal vector with 'X' in a circle) and a second normal vector straight out of the plane (the normal vector not shown, which would have a '·' in a circle). Here, when the right-hand rule of vectors is applied, the large articulation 500 can be determined as a clockwise articulation that selects the first normal vector into the measurement plane as the correct normal vector. Accordingly, the normal vector can indicate a direction of articulation.

Applying Equation (2) to the large articulation 500, the numerator term ($v_{ref} \times v_t$) results in a vector coming out of the plane of the drawing page since the pointing vector, $v_t$, is to the counterclockwise (e.g., left) of the reference vector, $v_{ref}$. As described, the normal vector, n, into the measurement plane can indicate that the pointing vector was reached through clockwise articulation. Since the normal vector is in the opposite direction of the ($v_{ref} \times v_t$) term, inner product of the normal vector and the term results in the numerator of the inverse tangent as a negative value. Searching for an inverse tangent of a negative value on an inverse tangent curve 620 of FIG. 6B, it can be seen that the computed signed angle is approximately −90 degrees. Combining the knowledge that the target points toward −90 degrees angle with the knowledge of clockwise articulation, the large articulation 500 may be correctly determined as a 270 degrees clockwise articulation by, for example, adding 360 degrees to the −90 degrees. Such articulations with angles greater than 180 degrees will be referred herein as wraparound articulations. A more detailed description of how the signed angle method can handle the wraparound angles will be provided in relation to FIGS. 10 and 11A-11C.

It is noted that the inverse tangent of Equation (2) is limited to an output angle range of −90 degrees to 90 degrees (or −π/2 to π/2 in radians) as shown with the inverse tangent curve 620 of FIG. 6B. In some embodiments, the limitation of the inverse tangent curve 620 may be addressed by utilizing other inverse tangent functions, such as arctan 2( ) function accessed as a part of Python Numpy standard library. Other readily available application programming interfaces or programming libraries may supply the arctan 2( ) function. The arctan 2( ) function can estimate a signed angle in a full 360 degrees range, from −180 degrees to 180 degrees (or −π to π in radians), as shown with its expanded curve plot in FIG. 6C. Accordingly, the signed angle computation can address both limitations of the unsigned angle computation. It will be understood that left-hand rule may be used instead of the right-hand rule so long as the rule is used and interpreted in a consistent manner.

Projected Signed Angle Computation

The unsigned angle method and signed angle method were described with an assumption that a plane of articulation (e.g., an articulation plane) matches with the measurement plane in which an articulation angle is to be determined between the reference vector and the pointing vector. In signed angle method, since the normal vector can represent a chosen measurement plane, selection of a different normal vector can result in different signed angle. The articulation plane can be a plane defined by articulation from the reference vector to the pointing vector. In other words, the reference vector and the pointing vector lie within the articulation plane. As the pointing vector can reflect any possible articulation of the distal end 442 in real-time, the articulation plane can vary in real-time based on the pointing vector. The measurement plane can be a plane of a coordinate system and typically remains unaffected by an articulation of the pointing vector.

Often, articulations are multiplanar involving articulation over multiple axes of the coordinate system. For example, the articulation plane defined by a reference vector and a pointing vector may simultaneously involve a first degree of articulation along a first axis and a second degree of articulation along a second axis (e.g., up and right instead of just up or just right) and involve multiple measurement planes. Accordingly, the articulation plane and the measurement plane may not exactly match in many instances. The mismatch may cause inaccurate estimation of the angle, as will be described in greater detail below.

Figure 7A:
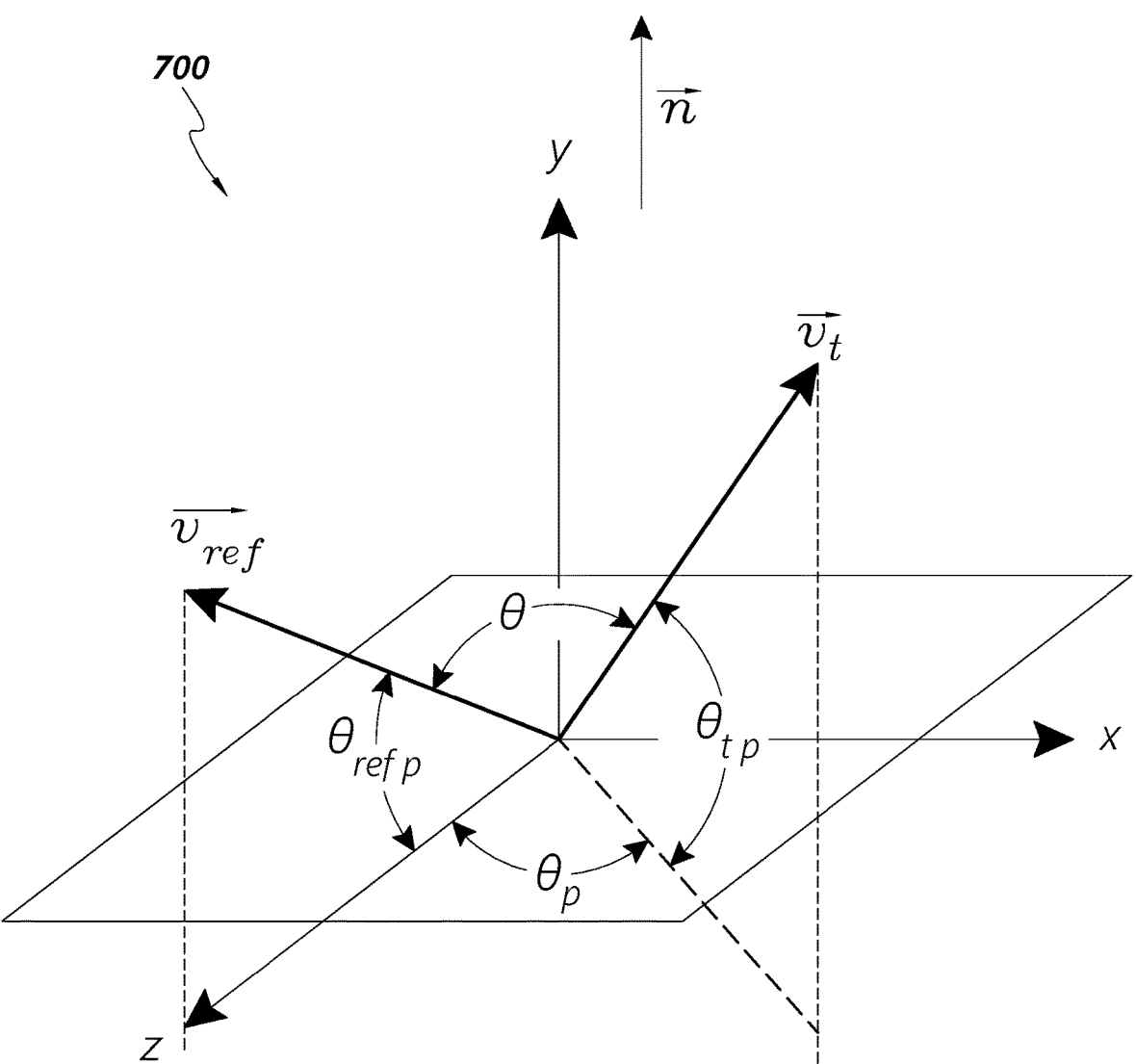
FIGS. 7A-7B illustrate example mismatches between articulation planes and measurement planes, in accordance with one or more embodiments.

FIG. 7A illustrates an example mismatch 700 between an articulation plane and a measurement plane. The measurement plane may be defined by XZ-plane and represented with a normal vector, n, which is parallel to Y-axis. The example mismatch 700 illustrates a counterclockwise articulation from a reference vector, $v_{ref}$, to a pointing vector, $v_t$. The articulation plane can be defined as a plane including both the reference vector and the pointing vector. The unsigned angle method and signed angle methods estimate an articulation plane angle, θ, in the articulation plane.

In many instances, the medical system 100 is interested in determining an articulation angle, $\theta_p$, as measured with respect to a chosen measurement plane but not the articulation plane. As mentioned, the measurement plane may be a plane of a coordinate system. As an example, the medical system 100 may represent articulation of the pointing vector in the coordinate system as a yaw-articulation with a measurement plane angle, $\theta_p$ (where p stands for projected), followed by a pitch-articulation of a projected pointing vector angle, $\theta_{t,p}$. Both $\theta_p$ and $\theta_{t,p}$ may be more relevant to the medical system 100 than the articulation plane angle, θ, due to their convenience of reference to the coordinate system. Thus, when the articulation plane and the measurement plane do not match, the articulation plane angle, θ, may not serve as the best indicator of an articulation angle.

Figure 7B:
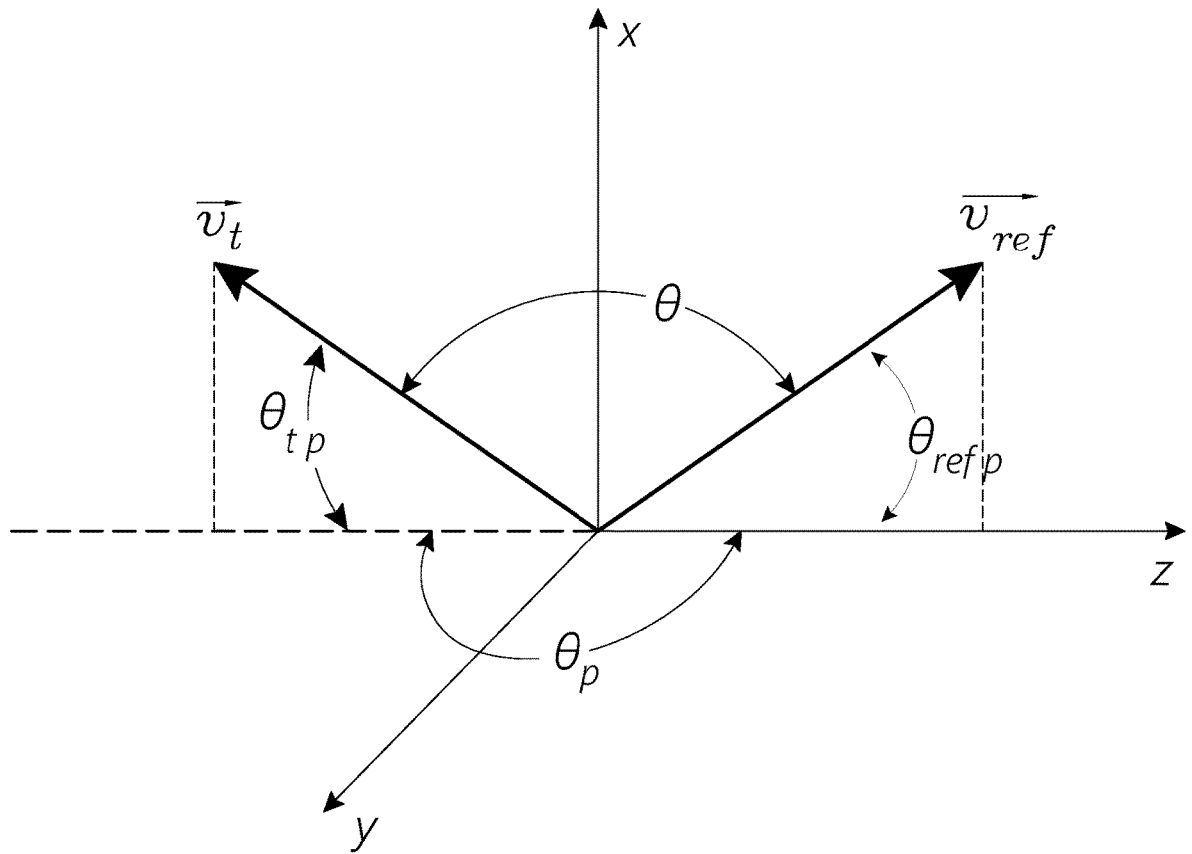

FIG. 7B illustrates another example mismatch 800 that is more of a corner case than the example mismatch 700 in FIG. 7A. Here, a reference vector, $v_{ref}$, and a pointing vector, $v_t$, in the XZ-plane. In the ZY-plane, the distal end 442 has completed a 180 degree sweep. The unprojected signed method will compute an articulation plane angle, θ, which clearly does not correctly reflect the 180 degrees sweep. In contrast, a measurement plane angle, $\theta_p$, computed based on the projected reference angle, $\theta_{ref,p}$, and the projected pointing angle, $\theta_{t,p}$, does reflect the correct 180 degrees sweep.

Projected signed angle method can provide estimations of the measurement plane angle, $\theta_p$, which may serve as a better indicator. The method can project and normalize the reference vector and the pointing vector onto the measurement plane as a projected reference vector, $v_{ref\ p}$, and a projected pointing vector, $v_{t,p}$. Then the method can estimate the measurement plane angle, $\theta_p$, as an angle between the two projected vectors. It is noted that reference vectors and pointing vectors of the unsigned angle method can be, like the vectors of the signed angle method, similarly projected onto the measurement plane for estimation of the unsigned measurement plane angle. While the projections can be used for both unsigned and signed angle methods, the present disclosure will focus on the projected signed angle method.

The method can use an altered Equation (2) using the two projected vectors instead of the original vectors, for example, using the following relationship:

$$\theta_p = \tan^{-1}\frac{(v_{refp} \times v_{tp}) \cdot n}{v_{refp} \cdot v_{tp}} \qquad \text{Equation (3)}$$

where a normal vector, n, may be a unit vector normal to the plane of measurement, and $v_{refp}$ and $v_{tp}$ may be unit vectors computed as:

$$v_{refp} = \frac{v_{ref} - (v_{ref} \cdot n)n}{\|v_{ref} - (v_{ref} \cdot n)n\|}$$

and $$v_{tp} = \frac{v_t - (v_t \cdot n)n}{\|v_t - (v_t \cdot n)n\|}$$

It is noted that, while the reference vector and the pointing vector are projected onto the measurement plane, the coordinate system may have other measurement planes (e.g., an YZ-plane for pitch in addition to the XZ-plane for yaw in FIG. 7A) and, by projecting respective vectors onto the other measurement planes, angles for those measurement planes may be computed and used for other applications. A skilled user could use the same pointing vector and one or multiple reference vectors as well as multiple measurement planes (and corresponding normal vectors) to characterize or control the state of the distal end 442 in detail.

Figure 8:
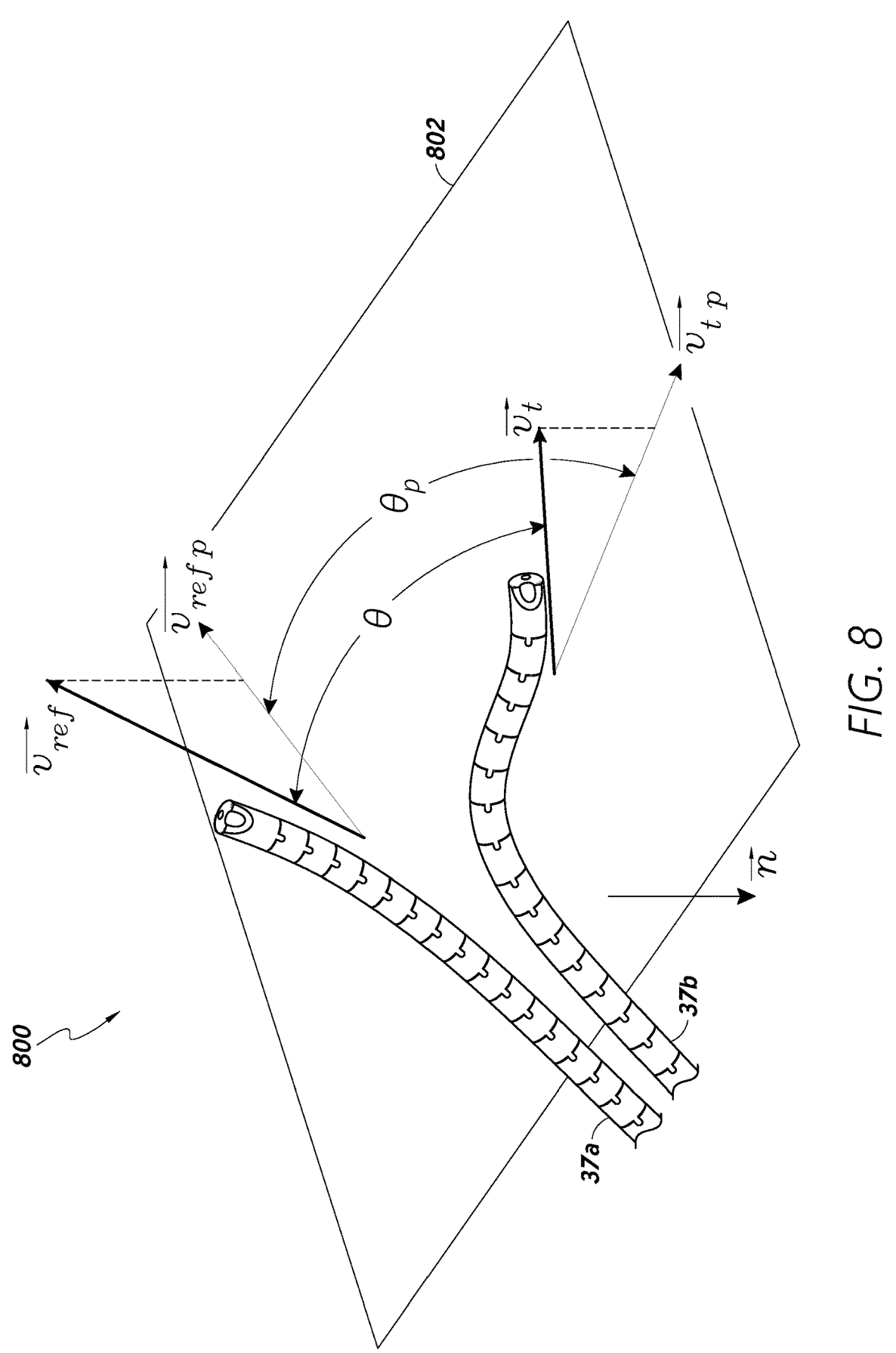
FIG. 8 illustrates an example application of a projected signed angle computation, in accordance with one or more embodiments.

FIG. 8 illustrates an example application 800 of the projected signed angle method. Specifically, FIG. 8 illustrates an articulation of the flexible elongated body 37 from the reference vector, $v_{ref}$, to the pointing vector (e.g., a new state where the tip points along vector), $v_t$. The articulation is in an articulation plane defined by the reference vector and the pointing vector and the (unprojected) signed angle method of Equation (2) can compute the articulation plane angle, $\theta$.

For the projected signed angle method, the reference vector is projected onto a measurement plane 802 as a projected reference vector, $v_{refp}$, and the pointing vector is similarly projected onto the measurement plane 802 as a projected pointing vector, $v_{tp}$. Either of the vectors may be normalized. The measurement plane 802 can be represented by a normal vector, n, which is downward to reflect a clockwise articulation of the flexible elongated body 37 from the projected reference vector to the projected pointing vector in the measurement plane 802. In contrast with the unprojected signed angle method, which computed the articulation plane angle, $\theta$ (shown off the measurement plane 802), using a first normal vector based on the articulation plane, the projected signed angle method computes a measurement plane angle, $\theta_p$ (on the measurement plane 802), using a second normal vector based on the measurement plane 802.

It is noted that the projected signed angle method replaces the reference vector and the pointing vector of the signed angle method with projected (and, in some embodiments, normalized) versions of the vectors. Accordingly, various observations made with the signed angle method may be similarly applicable to the projected signed angle method. In other words, the observations made thus far in relation to Equation (2) can apply to Equation (3). For instance, both methods can estimate articulation angles in full 360 degrees range, thus capable of identifying and handling wraparound angles.

Figure 9:
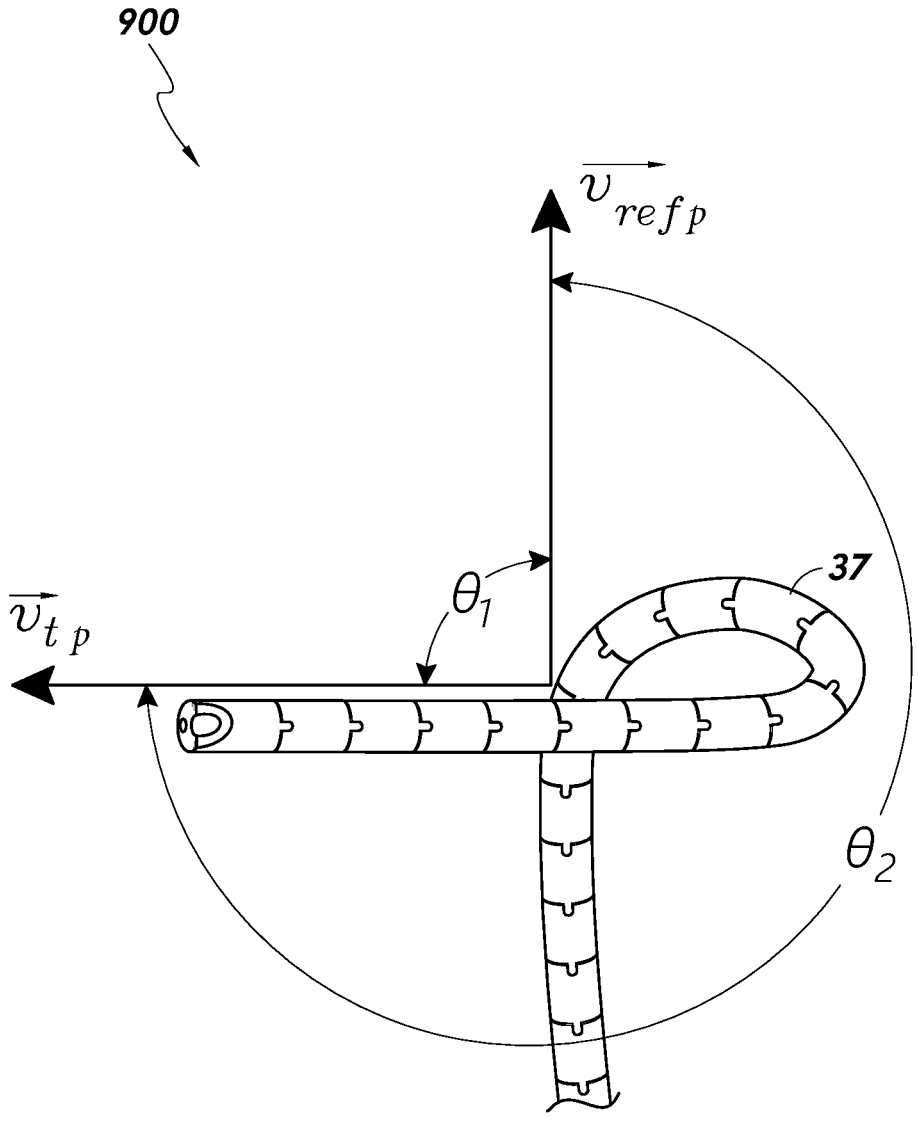
FIG. 9 illustrates an example wraparound angle and its vectors, in accordance with one or more embodiments.

FIG. 9 illustrates example articulations 900 represented with a projected reference vector, $v_{ref\ p}$, and a projected pointing vector, $v_{t\ p}$. It is observed that two distinct articulations may result in the depicted projected pointing vector: a counterclockwise 90 degrees articulation, $\theta_1$, and a clockwise 270 degrees articulation, $\theta_2$. Equation (3) can be applied to the two distinct articulations $\theta_1$ and $\theta_2$ in the similar manner as Equation (2) applied to the example large articulation 500 of FIG. 5 to compute −90 degrees articulations. Like Equation (2), Equation (3) may determine or maintain a normal vector indicative of articulation direction. For instance, the normal vector can be into the page for the clockwise 270 degrees articulation, $\theta_2$. and out of the page for the counterclockwise 90 degrees articulation, $\theta_1$, when based on the right-hand rule. When the normal vector indicates a clockwise articulation, the computed-90 degrees should be recognized as a wraparound scenario (e.g., crossed 180 degrees articulation during clockwise articulation to 270 degrees) and may be unwrapped by adding 360 degrees to compute the correct clockwise 270 degrees articulation, $\theta_2$. A more detailed description of how the projected signed angle method can handle the wraparound angles will be provided in relation to FIGS. 10 and 11A-11C.

Signed Angle Computation Flow Diagram

Figure 10:
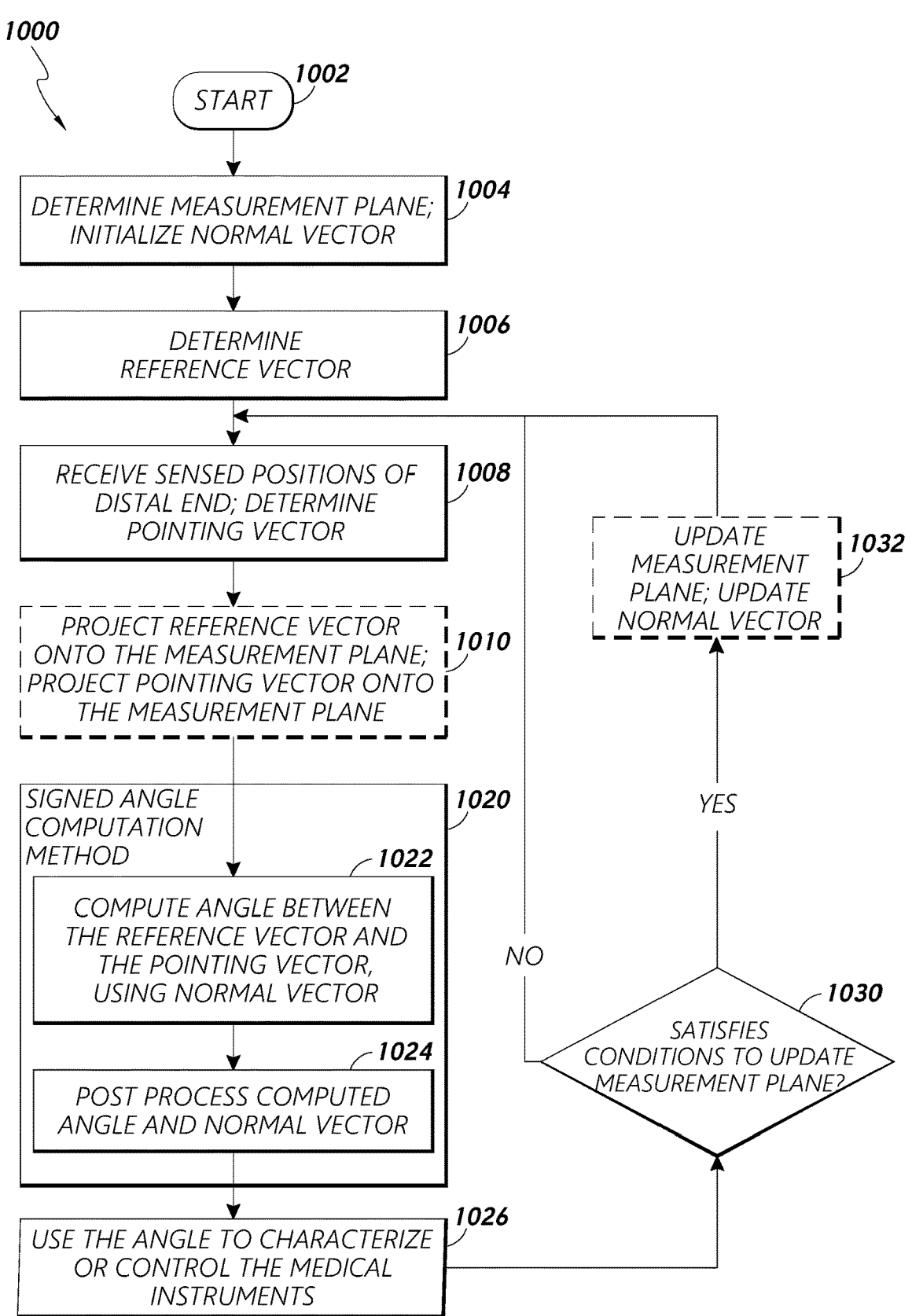
FIG. 10 illustrates a flow diagram of a process for signed angle methods, unprojected or projected, in accordance with one or more embodiments.

FIG. 10 is a flow diagram of a process 1000 for signed angle methods, unprojected or projected, in accordance with one or more embodiments. The process 1000 can unwrap a large articulation angle, reverse normal vector, and/or update measurement plane. The process 1000 will be described in relation to FIG. 11. A first scenario 1120 of FIG. 11 represents a wraparound scenario. A second scenario 1140 of FIG. 11 represents a normal vector reversal scenario.

As shown, the first scenario 1120 and the second scenario 1140 are described based on a reference coordinate system 1100 illustrated with visual and numerical representations of a normal vector (n) in relation to a measurement plane, a reference vector ($v_{ref}$), and a pointing vector ($v_t$). While the reference coordinate system 1100 depicts Cartesian coordinate system, it is to be understood that present disclosure contemplates other reference coordinate systems including polar coordinate system, cylindrical and spherical coordinate systems, homogeneous coordinate system, or the like.

At block 1002, the process 1000 can start. In some embodiments, the process 1000 may be executed as part of an initialization process for the medical instrument 40 or in response to some user input.

At block 1004, the process 1000 can involve determining, choosing, or selecting a measurement plane and initializing a normal vector. The determination of the measurement plane and initialization of the normal vector will be described in greater detail in relation to FIG. 12. Here, it will be understood that a measurement plane and a normal vector of the reference coordinate system 1100 will be used in connection with the process 1000. As described, the measurement plane does not have to be exactly aligned with the articulation plane. However, for convenience in describing wraparounds and normal vector reversal scenarios, it will be assumed that the distal end 442 is articulated on the measurement plane (e.g., articulation plane is the same as the measurement plane).

At block 1006, the process 1000 can involve determining, choosing, or selecting a reference vector. In one aspect, the reference vector may have been previously determined in a laboratory setting (and stored in memory) for a specimen of the medical instrument 40 that was in its unbent state or in another known state (or equivalently the distal end was in some known pose). In another aspect, the reference vector may be determined in-the-field by the medical system 100, based on an initial sensed pose of the distal end 442. In the reference coordinate system 1100, the reference vector is selected as a vector parallel to the measurement plane (e.g., YZ-plane) such that the projected reference vector is the same as the reference vector (e.g., $v_{ref\ p}=v_{ref}$). A skilled person would readily understand that the selection of the reference vector is for convenience in descriptions only and any reference vector can be selected.

At block 1008, the process 1000 can involve receiving one or more sensed poses of the distal end 442 of the medical instrument flexible elongated body 37. The sensed pose may be one of several sensed poses received as a time sequence, and each may depend on or correspond to how the flexible elongated body 37 is bent or articulated. The sensed pose may be produced by a pose tracking subsystem (e.g., a 3D pose tracking system including the EM field generator 18 and the sensor 403 configured as an EM sensor) described above.

Additionally, a pointing vector can be determined. As the flexible elongated body 37 articulates, the medical system 100 may update the measured pointing direction vector of the distal end of the flexible elongated body 37. The pointing vector may be defined as pointing along and to a tip of the distal end 442 and may be updated for each sample of the sensed pose of the distal end. In the example reference coordinate system 1100, the pointing vector may be a unit vector parallel to the measurement plane (e.g., YZ-plane) such that the projected pointing vector is the same as the pointing vector (e.g., $v_{t\ p}=v_t$). A skilled person would readily understand that the selection of the presented vector is for convenience in descriptions only and any pointing vector can be used.

At block 1010, the process 1000 can optionally involve projecting the reference vector and the pointing vector onto the measurement plane. This block 1010 is optional in the sense that, in the absence of the projections, the process 1000 can become the unprojected signed angle method. Inclusion of the projections converts the signed angle method to the projected signed angle method.

As described in relation to the projected signed angle method described in relation to FIGS. 7 and 8, the reference vector and the pointing vector can be projected onto the measurement plane, which may be represented with a normal vector. The reference vector and the pointing vector may be normalized. In the reference coordinate system 1100, the projected reference vector ($v_{ref\ p}$) and the projected pointing vector ($v_{t\ p}$) are the projected vectors on the measurement plane (n), which has an out-of-plane normal vector.

I. Angle Computation

At block 1020, the process 1000 can involve performing the unprojected signed angle method or the projected signed angle method, depending on whether the optional block 1010 was performed. Additionally, at block 1020, the process 1000 can involve addressing wraparound scenarios and normal vector reversal scenarios. While below descriptions focus on projected vectors, those skilled in the art will appreciate that the descriptions are applicable to unprojected signed angle method so long as unprojected vectors are used in a consistent manner to replace the projected vectors from the descriptions.

Referring to FIG. 11, the reference coordinate system 1100 depicts the projected reference vector, the projected pointing vector, and the normal vector that are:

$$v_{refp} = \begin{bmatrix} 0 \\ 0 \\ 1 \end{bmatrix}, v_{tp} = \begin{bmatrix} 0 \\ -\sin\phi \\ \cos\phi \end{bmatrix}, n = \begin{bmatrix} 1 \\ 0 \\ 0 \end{bmatrix}$$

At block 1022, the process 1000 can involve computing an articulation angle between the unprojected/projected reference vector and the unprojected/projected pointing vector, using the normal vector. The articulation angle may be computed based on Equation (2) or (3).

Referring again to FIG. 11, the first scenario 1120 represents a wraparound scenario with a first articulation from 0 degrees to 135 degrees ($\phi_1$), followed by a second articulation to 225 degrees ($\phi_2$). The second scenario 1140 represents a normal vector reversal scenario with a third articulation from 225 degrees back to 15 degrees ($\phi_3$), followed by a fourth articulation to −15 degrees ($\phi_4$). For each of the articulations in FIG. 11, the articulation angles can be computed using Equation (2) or (3):

$$\phi_1: \theta_1 = \tan^{-1}\left(\frac{\sin 135}{\cos 135}\right) = 135, \quad n = \begin{bmatrix} 1 \\ 0 \\ 0 \end{bmatrix}$$

$$\phi_2: \theta_2 = \tan^{-1}\left(\frac{\sin 225}{\cos 225}\right) = -135, \quad n = \begin{bmatrix} 1 \\ 0 \\ 0 \end{bmatrix}$$

$$\phi_3: \theta_3 = \tan^{-1}\left(\frac{\sin 15}{\cos 15}\right) = 15, \quad n = \begin{bmatrix} 1 \\ 0 \\ 0 \end{bmatrix}$$

$$\phi_4: \theta_4 = \tan^{-1}\left(\frac{\sin(-15)}{\cos(-15)}\right) = -15, \quad n = \begin{bmatrix} 1 \\ 0 \\ 0 \end{bmatrix}$$

At block 1024, the process 1000 can involve post processing computed angle and normal vector. The computed angles (e.g., $\phi_1$, $\phi_2$, $\phi_3$, $\phi_4$, etc.) may be evaluated to determine (i) whether the articulation angle is a wraparound angle with a wraparound conditional logic and/or (ii) whether there is a normal vector reversal in relation to the projected reference vector on the measurement plane with a normal vector reversal conditional logic.

I. A. Wraparound Conditional Logic

The wraparound conditional checks (i) whether the articulation angle is negative (e.g., $\theta < 0$) and (ii) whether an absolute value of the articulation angle is greater than a wraparound threshold (e.g., $|\theta| > \theta_{wraparound_{limit}}$). The condition may be satisfied when an articulation crosses 180 degrees resulting in a wraparound scenario. In some embodiments, the wraparound conditional may be written in pseudo-code as:

```
if ((θ<0) & (|θ|>θ_wraparound_limit)):

θ=360+θ                              Code (1)
```

Referring to the wraparound angle, $\phi_2$, the second articulation that starts at 135 degrees, crosses the 180 degrees, and moves toward 225 degrees can be plotted on the arctan 2( ) curve 640 of FIG. 6C. In the curve 640, the wraparound angle is arrived at by moving along a first trajectory 642 toward 180 degrees on the topmost curve, suddenly jumps to the bottommost curve when the arctan 2( ) outputs 180 degree to −180 degree switch, and moving along a second trajectory 644 away from −180 degrees on the bottommost curve. Thus, there was a sign change to a negative angle.

The wraparound threshold, $\theta_{wraparound_{limit}}$, can be selected as a value dependent on the medical system 100. In some embodiments, the wraparound threshold may be selected based on frequency of pointing vector sampling. For example, the pointing vector may be sampled several times per second and, based on control characteristics of the medical system 100, there may be a limit to how quickly articulation angle may change. For instance, if the articulation angle change is at most 30 degrees between samples, the wraparound threshold may be selected as being at least the maximum angle change per sample, i.e. 30 degrees.

Figure 11A:
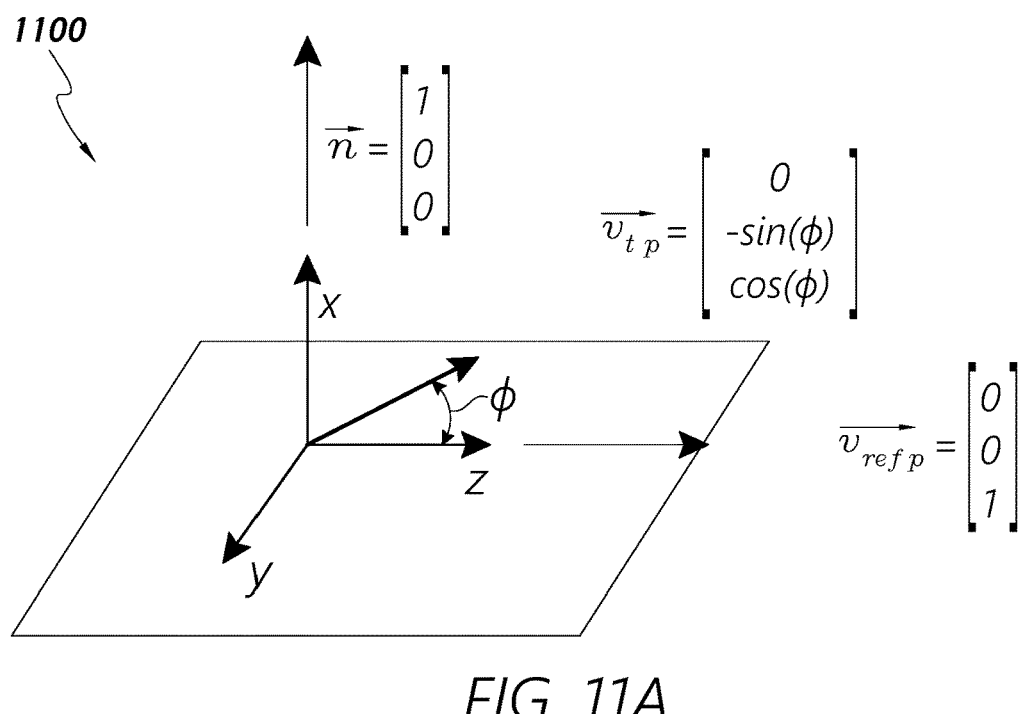
FIGS. 11A-11C illustrate a set of visual aids in connection with the flow diagram of FIG. 10, in accordance with one or more embodiments.
Figures 11B, 11C:
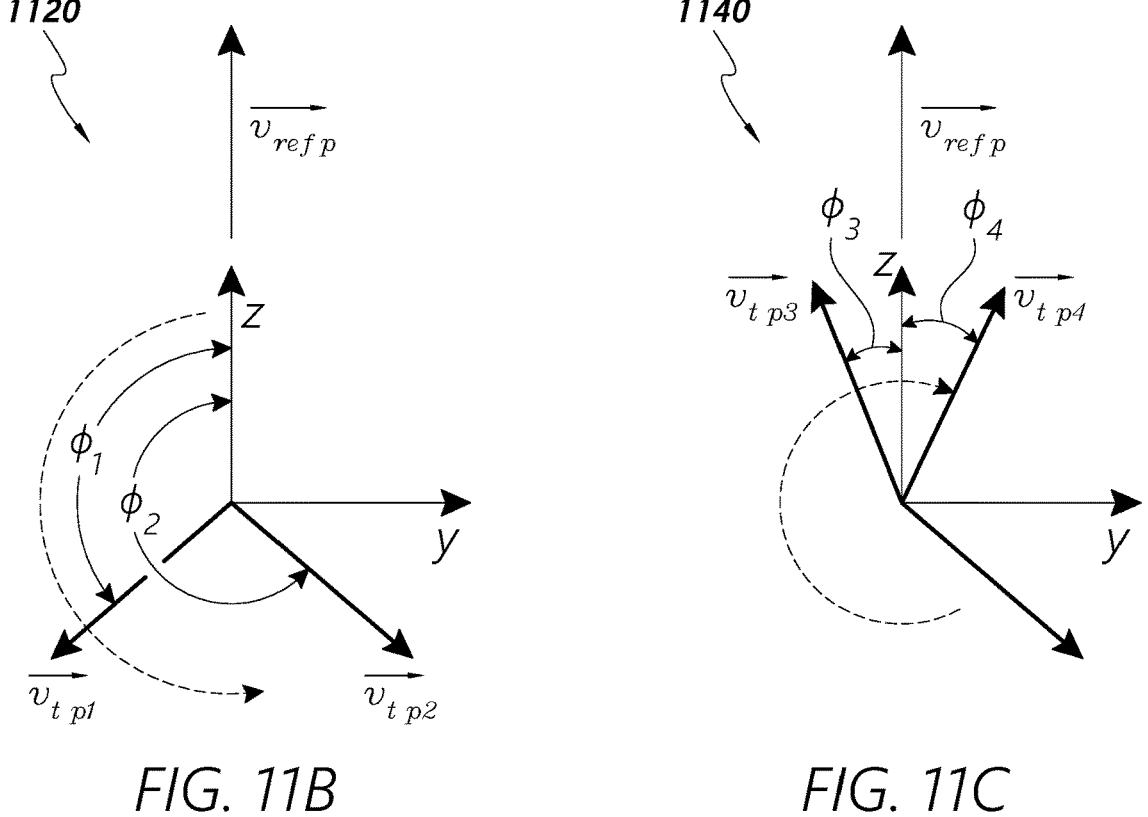

The articulation to 225 degrees, $\emptyset_2$, in FIG. 11A satisfies the wraparound conditional of Code (1), thus indicating a wraparound scenario. Assuming the wraparound threshold is 30 degrees, for example, the computed angle of −135 degrees is (i) negative and (ii) the absolute value 135 degrees is greater than the assumed wraparound threshold. When the wraparound conditional is satisfied, Code (1) unwraps a wraparound scenario by adding 360 degrees to the computed angle. Graphically, this is akin to adding $2\pi$ to the start of the second trajectory 644 (e.g., −180 degrees or −$\pi$) such that the start is connected to the end of the first trajectory 642 (e.g., 180 degrees or $\pi$). On the connected curve, the wraparound scenario can be correctly handled as continuously increasing articulation angle.

Referring back to the wraparound angle, $\emptyset_2$, 360 degrees is added to the computed angle of −135 degrees to provide 225 degrees. That is:

$$\emptyset_2: \theta_2 = -135 + 360 = 225, \quad n = \begin{bmatrix} 1 \\ 0 \\ 0 \end{bmatrix}$$

I. B. Normal Vector Reversal Conditional Logic

Normal vector reversal conditional may be examined when the wraparound conditional is not satisfied. The normal vector reversal conditional checks whether there has been a change in direction in the pointing vector in relation to the reference vector on the measurement plane. There may be a directional change when articulation begins with a clockwise angle but ends with a counterclockwise angle, and vice versa. Note that the cross multiplicative term (e.g., $v_{ref}$ $_p \times v_{tp}$) of Equation (2) or (3) changes sign when the pointing vector changes its direction in relation to the reference vector, thereby computing in a negative angle. In some embodiments, the normal vector reversal conditional may be written in pseudo-code as:

elseif (θ<0):

θ=|θ| n=−n                           Code (2)

Referring to the directionally reversed angle, $\emptyset_4$, the fourth articulation that starts at 15 degrees, crosses 0 degrees, and moves toward −15 degrees can be plotted on the arctan 2( ) curve 640 of FIG. 6C as following a third trajectory 646.

The articulation to −15 degrees, $\emptyset_4$, satisfies the normal vector reversal conditional. Assuming the wraparound threshold is 30 degrees, the computed angle of −15 degrees is not large enough in magnitude to satisfy the wraparound conditional although it satisfies the normal vector reversal conditional. When the normal vector reversal conditional is satisfied, (i) the computed angle is made positive and (ii) the normal vector is reversed (i.e., n=−n). Combined, the logic reverses the direction of the normal vector to update articulation direction and ensures that the computed angle is positive in relation to the updated articulation direction.

Referring back to the directionally reversed angle, $\emptyset_4$, the computed angle of −15 degrees may be replaced with the positive angle of 15 degrees and the normal vector is reversed. That is:

$$\emptyset_4: \theta_4 = |-15| = 15, \quad n = \begin{bmatrix} -1 \\ 0 \\ 0 \end{bmatrix}$$

In some embodiments, as described, any computed angles may be represented as an absolute (e.g., positive) angle since the medical system 100 determines and maintains both the computed angle value and the correct articulation direction with the normal vector. That is, the computed angle may always be positive rotation about the normal vector according to the right-hand rule. When shifting from clockwise to counterclockwise, or vice versa, the computed angle may not become negative but the normal vector may be reversed to denote the change in the articulation direction. Advantageously, this approach avoids potential confusion about what convention is used when a negative angle is provided as a clockwise or a counterclockwise articulation.

I. C. Default Scenario

For the other computed angles that do not satisfy the wraparound conditional or the normal vector reversal conditional (e.g., 135 degrees, $\emptyset1$, and 15 degrees, $\emptyset_3$), no adjustments are needed.

At block 1026, the process 1000 can involve using the resulting computed angle for either generating a new command for controlling the flexible elongated body 37 or characterizing the flexible elongated body 37 in association with an existing command.

II. Measurement Plane Update

In some embodiments, the process 1000 can optionally involve updating the measurement plane. It is important to discuss and differentiate between various planes that affect computation of the signed angle. The present disclosure distinguishes three different types of planes: an articulation plane, a measurement plane, and a control plane. As mentioned, the articulation plane can be a plane that contains both the reference vector and the pointing vector. Since the pointing vector can reflect any possible articulation of the distal end 442 in real-time, the articulation plane can vary in real-time based on the pointing vector.

The measurement plane can be a plane defined by a kinematic model, a collection of features within a subject's anatomy (e.g., a plane based on a detected orientation of a kidney, lung, heart, etc., or any classical planes including anterior/posterior, sagittal/coronal plane, traverse plane, medial/lateral, etc.), historical data collected while the medical system 100 is being used, expected behavior of the flexible elongated body 37 and the distal end 442 as measured by a sensing solution with a known coordinate system, or the like. For example, a kinematic model may define a horizontal plane (e.g., the YZ-plane of the reference coordinate system 1100 in FIG. 11A) for the yaw axis 402 and/or a vertical plane (e.g., the XZ-plane of the reference coordinate system 1100 in FIG. 11A) for the pitch axis 404 of FIG. 3, either of which may be the measurement plane. The normal vector can be a vector perpendicular to the measurement plane and, accordingly, may have two opposite representations on the measurement plane. Unlike the articulation plane, the measurement plane can be a type of a reference plane in the sense that the measurement plane stays unaffected by an articulation of the pointing vector (e.g., articulation of the distal end 442).

The control plane can be a plane defined by control or actual behavior of the flexible elongated body 37 and the distal end 442. The control plane can be defined based on actual articulation responses. In other words, how the medical instrument 40 actually manifests pitch and yaw, for example, can define the control plane. For example, when commands to articulate only pitch based on the kinematic model were given, the resulting actual articulation may (i) include some yaw articulation in addition and/or (ii) effectuate lesser or greater pitch articulation than commanded. Unlike the articulation plane and like the measurement plane, the control plane is a type of a reference plane in the sense that the control plane stays unaffected by an articulation of the pointing vector.

Thus far, all descriptions assumed that the measurement plane and the control plane are matched and that expected behavior and actual behavior are synchronized. However, actual behavior of the medical instrument 40 may be shifted, translated, rotated, etc. from expected behavior of the kinematic model. In other words, the control plane does not necessarily have to match or be aligned with the measurement plane. Some degree of mismatch may be due to inherent discrepancy between a model and behavior including, component variances and tolerances variations causing system-by-system differences, wear and tear causing a single system control plane to become desynchronized, or the like. In some instances, the mismatch may be caused or aggravated by configuration or operation of the medical instrument 40 including, a pre-articulated flexible elongated body 37 docked to an end effector causing the model/behavior mismatch, a "roll" maneuver along the longitudinal axis 406 in FIG. 3 potentially introducing the mismatch, or the like.

The mismatch makes accurate determination of a normal vector challenging. For example, the mismatch may manifest as a normal vector of the measurement plane, which is used to characterize articulation, being different from a normal vector of the control plane, which is used to articulate. As the signed angle methods rely on accurate normal vector in their formulae, computed angles may be incorrect unless this mismatch is addressed. The mismatch may be reduced or eliminated by updating the measurement plane such that the measurement plane becomes aligned with the control plane.

In particular, determination of the measurement plane to use can be challenging when the distal tip 442 is operating in a new environment. In this scenario, a guessed measurement plane or a predicted measurement plane can be used and later be updated as more articulation data is made available. For example, historical command and movement data can be used to identify a plane of a patient's anatomy or a plane that best matches a given type of input command (e.g., a plane of best fit to motion data).

Regarding the plane based on the patient's anatomy, FIG. 3 illustrates a kidney which may define a plane, for example. Suppose the distal end 442 is navigated to a point at the center of a kidney stone. The position may be tagged as a datum and the instantaneous measured pose of the distal end 442 may be designated as a reference vector. Two planes, a left-right and an up-down planes, may be defined. These planes could be obtained either through using historical data, transformations, or other external measurements. Throughout a treatment of a kidney stone in the kidney, for example, the articulation angle of the distal end 442 may be computed respect to each of these planes. In some embodiments, such planes may be determined based on one or more sensors. For example, images captured by the distal end 442 may be used to identify one or more features of an anatomy (e.g., the plane of a kidney) and measured planes may be fitted to the features.

At block 1030, the process 1000 can optionally involve evaluating whether the measurement plane should be updated (by changing the measurement plane and/or changing the sign of the normal vector) such that the computed angle better matches a desired angle on the measurement plane (e.g., $\theta_p$ of FIGS. 7A, 7B, and 8). The evaluation can involve one or more criteria. One example criterion may be whether enough articulation data (e.g., articulation history) have been collected to update the measurement plane by fitting a plane to the articulation data. Articulation data may comprise a time sequence of one or more articulation or a time sequence of one or more articulation planes, as described in relation to FIG. 5. The criterion may prevent the medical system 100 from updating the measurement plane based on insufficient of articulation data. Another example criteria may be whether certain direction, amount, and/or sequence of articulation have been performed. Yet another example criteria may be whether it is likely that all mismatch, as tracked based on some error metric, may have been addressed. Yet another example criteria may be whether the medical system 100 has been operational for some defined time duration. The evaluation criteria will be described in greater detail in relation to FIG. 12.

When at least one of the evaluation criteria for updating the measurement plane is satisfied, then the process 1000 can proceed to block 1032 to perform updating the measurement plane. Otherwise when none of the evaluation criteria is satisfied, then the process 1000 can proceed to block 1008 to when a new tip pointing vector is supplied to compute the next angle.

At block 1032, the process 1000 can involve updating the measurement plane and, based on the updated measurement plane, updating the normal vector. In some instances, block 1032 may involve updating the normal vector without updating the measurement plane. After the measurement plane and the normal vector are updated, the process 1000 may continue to block 1008 to determine the next pointing vector for the next angle computation. At block 1010, the reference vector and the next pointing vector may be projected onto the updated measurement plane. The measurement plane update process will be described in greater detail in relation to FIG. 12.

The process 1000 may repeat blocks 1008-1032 when a new current sensed pose is received. It should be understood that the process 1000 may be altered to include or exclude some of the blocks. For example, the process 1000 may be altered to estimate an articulation angle using signed angle method of Equation (2) when projection steps of block 1010 are removed. The process can also be altered to include updates to the reference vector as deemed appropriate by a skilled user.

In some embodiments, multiple instances of the process 1000 may be executed in parallel simultaneously to compute articulation angles on multiple measured planes. That is, one process may measure a compound articulation of the distal end 442 in the "left-right" direction on a first measurement plane and another process may measure the articulation in the "up-down" direction on a second measurement plane. This may be an advantage of the projected signed angle method. A skilled person may measure the compound articulation first in a measurement plane that captures the left-right plane (the first measurement plane) motion of the distal end 442 and then perform another independent measurement with another measurement plane that captures the up down (the second measurement plane) motion of the distal end 442 to obtain a more clear picture of the compound articulation.

Measurement Plane and Normal Vector Update Flow Diagram

Figure 12:
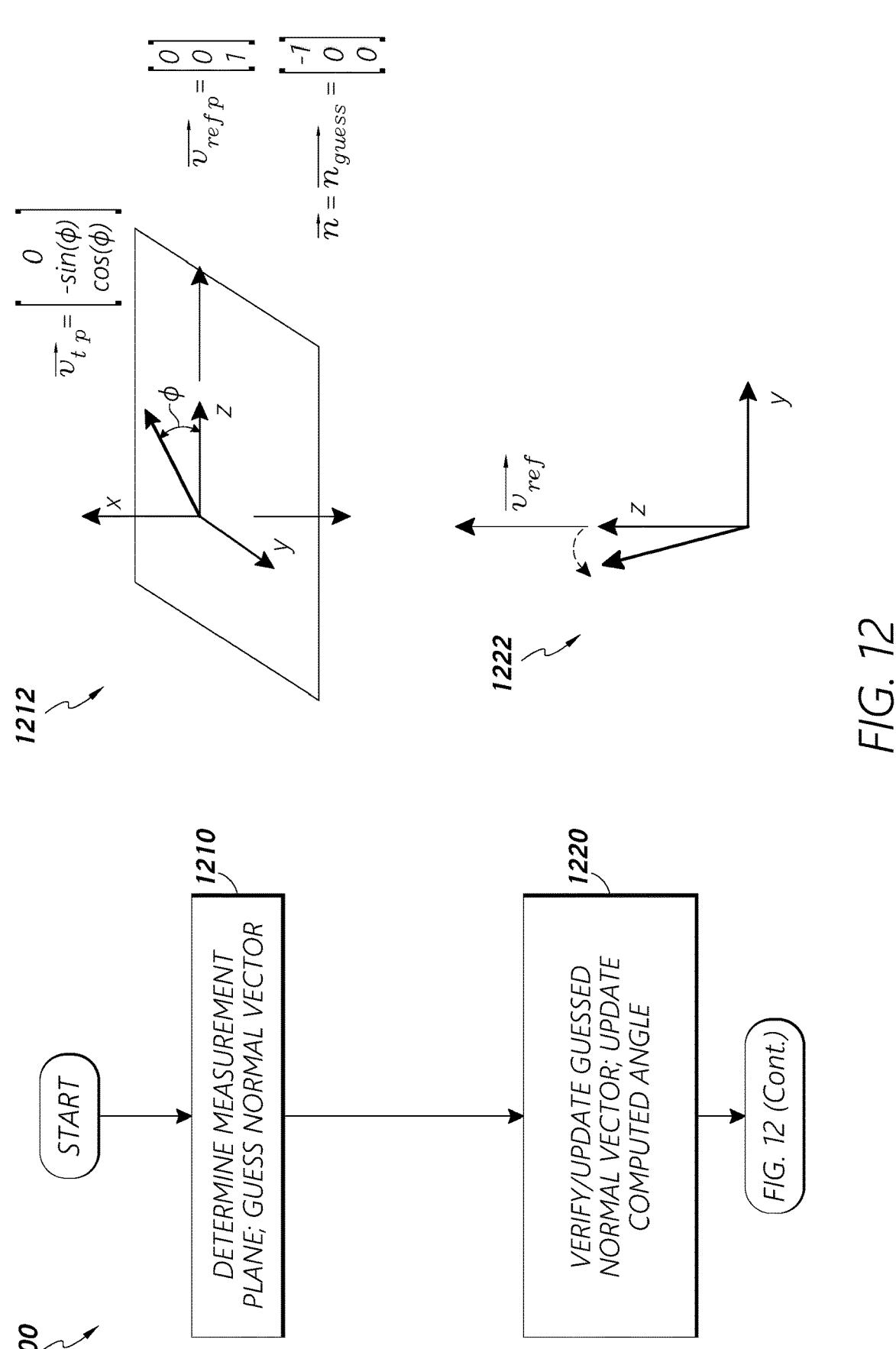
FIG. 12 illustrates a flow diagram of a process for updating the measurement plane and the normal vector, in accordance with one or more embodiments.
Figure 12:
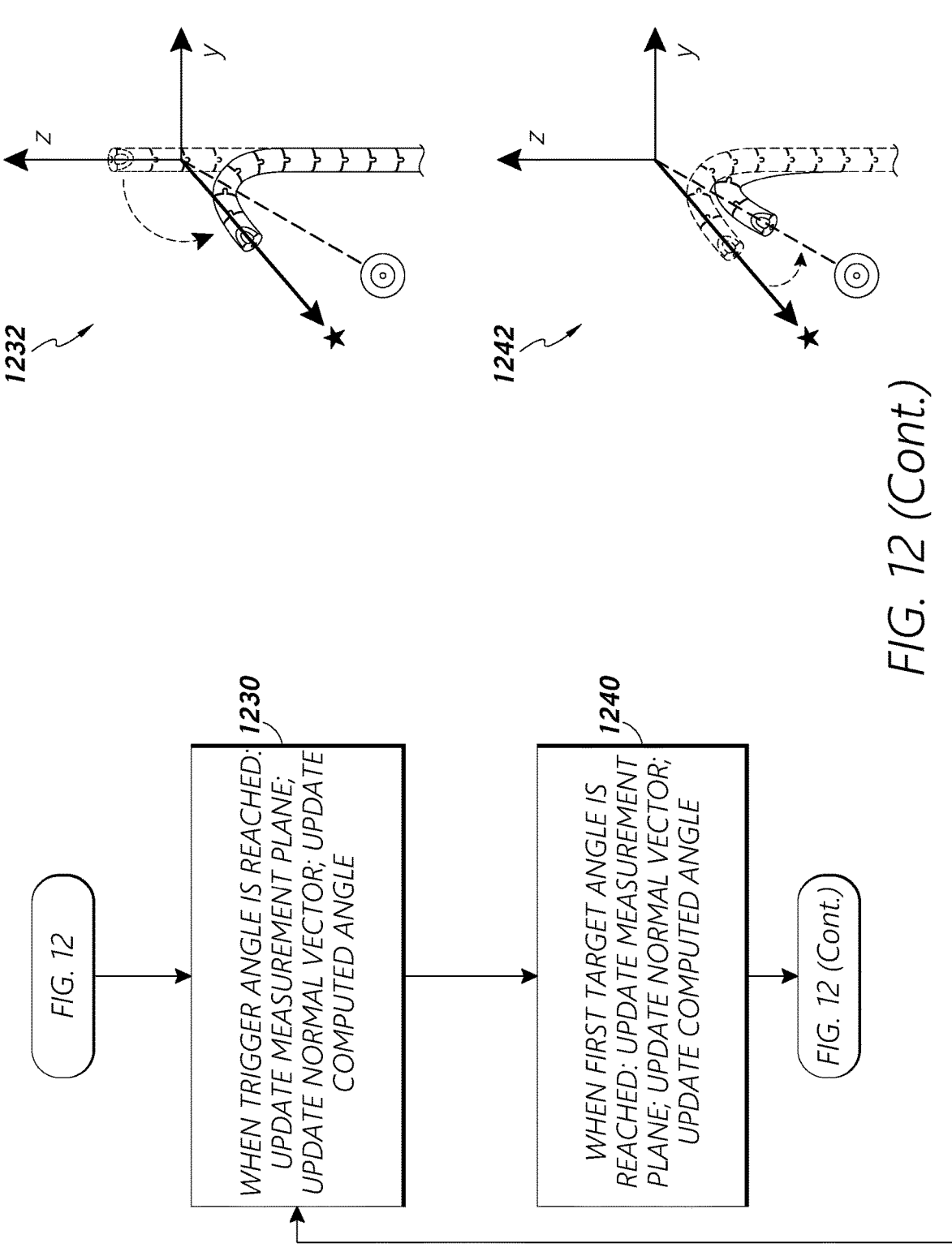
Figure 12:
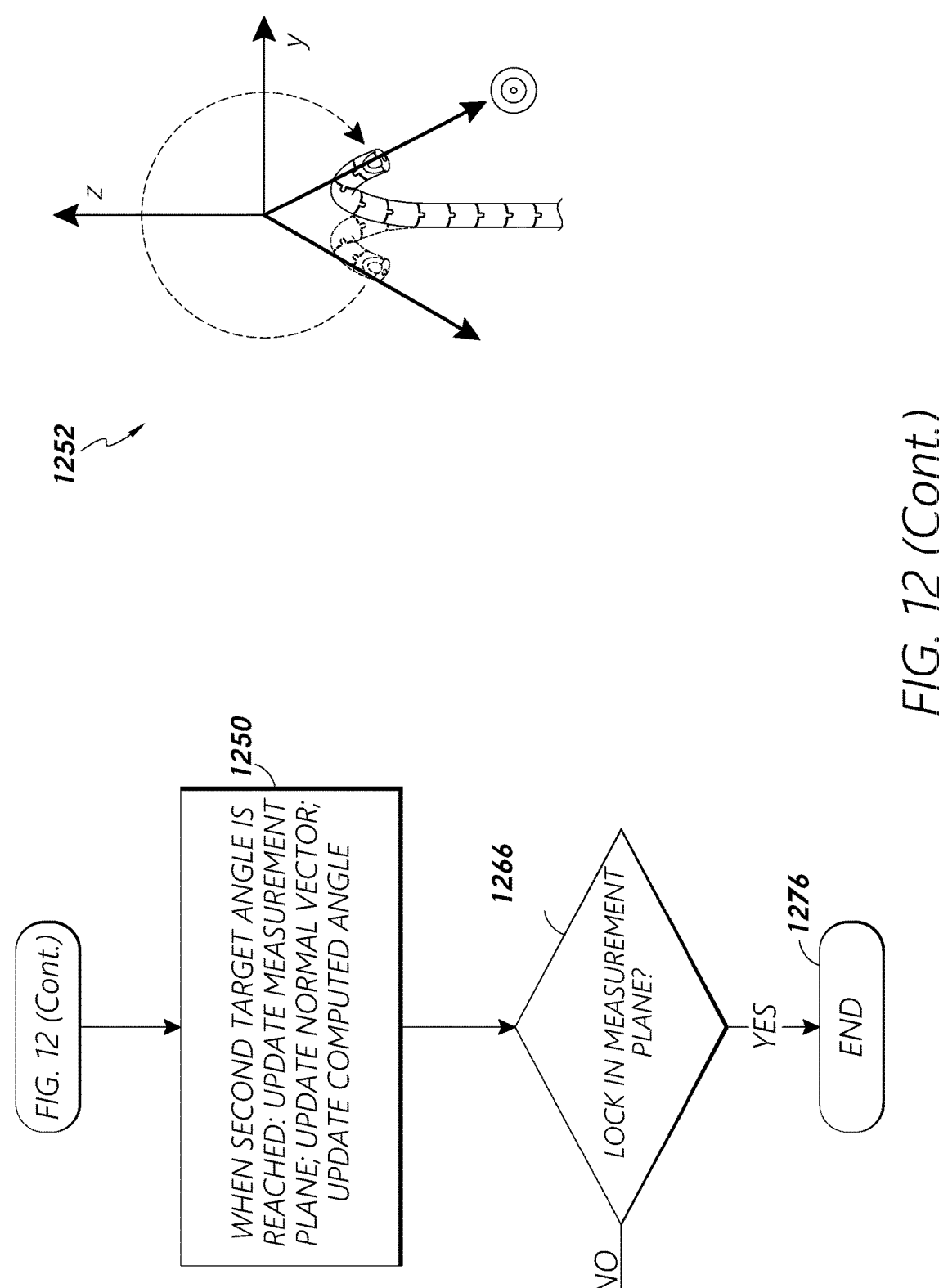

FIG. 12 is a flow diagram of a process 1200 for updating the measurement plane and the normal vector, in accordance with one or more embodiments. The process 1200 may describe inner workings of the blocks 1030 and 1032 of FIG. 10 and may supplement its process 1000. The right side of FIG. 12 provides visuals for when the measurement plane and the normal vector should be updated. The process 1200 may be executed as part of an initialization process for the medical instrument 40 or in response to some user input. In some other embodiments, the process 1200 may be executed as a background process or a thread.

At block 1210, the process 1200 can involve determining a measurement plane and guessing a normal vector. Block 1210 may be executed before any articulation is commanded, such as at initialization or reset, and the measurement plane may be a default measurement plane (e.g., based on a kinematic model, or an expected orientation of the device with respect to other landmarks in the operating area). In some embodiments, block 1210 is executed as part of or in connection with block 1004 of FIG. 10 where the measurement plane is determined and the normal vector is initialized. It is noted that the measurement plane may be associated with two normal vectors, one normal vector that is out of the measurement plane when viewed facing the measurement plane (e.g., n shown with the reference coordinate system 1100 of FIG. 11) and the other normal vector that is into the measurement plane from the same view (e.g., n shown with another reference coordinate system 1212 of FIG. 12). Either normal vector may be selected as an initial guess.

At block 1220, for an early computed signed angle (e.g., a computed angle from block 1022 of FIG. 10), the process 1200 can involve verifying the initial guessed normal vector and, when appropriate, updating the normal vector and the computed signed angle. The verification can guard against a scenario where the initial guessed normal vector points in the opposite direction. "Early" here is used to describe angles computed based on the initial guessed normal vector and the default measurement plane, which may be the first computed angle after a first sensed non-zero pointing vector.

Verification can involve determining whether computed signed angle is positive based on the initially guessed normal vector. When the verification fails (e.g., the computed angle is negative), indicating that the initial guess was wrong and that the normal vector should be the other normal vector, then the guessed normal vector is reversed. The verification can work accurately since, during early articulation resulting in the early computed signed angle, wraparound scenario is unlikely as the medical instrument 40 has just started articulating. Thus, any negative articulation is likely due to wrongly guessed normal vector. In some embodiments, the verification and update logic can be written in pseudo-code as:

```
if (θ<0):

θ=|θ| n=−n                            Code (3)
```

It is observed that the above pseudo-code bears some resemblance with the normal vector reversal conditional of Code (2) described in relation to block 1032 of FIG. 10, which is to be expected as both codes aim to determine a correct normal vector.

Applying Code (3), when the guessed normal vector is n shown in the reference coordinate system 1212 of FIG. 12, vectors for an articulation angle $\emptyset=1$ (as shown with a first articulation 1222) are:

$$v_{refp} = \begin{bmatrix} 0 \\ 0 \\ 1 \end{bmatrix}, \; v_{tp} = \begin{bmatrix} 0 \\ -\sin\emptyset \\ \cos\emptyset \end{bmatrix}, \; n_{guess} = \begin{bmatrix} -1 \\ 0 \\ 0 \end{bmatrix}$$

Computing the articulation angle with the signed angle method:

$$\emptyset_{computed} = \tan^{-1}\frac{(v_{refp} \times v_{tp}) \cdot n_{guess}}{v_{refp} \cdot v_{tp}} = \tan^{-1}\left(\frac{-\sin 1}{\cos 1}\right) = -1$$

Verification of the computed angle, $\emptyset_{computed}$, with Code (3) fails since the computed angle is negative. Thus, the normal vector and the computed angle are updated:

$$\emptyset_{computed} = |-1| = 1, \quad n = \begin{bmatrix} 1 \\ 0 \\ 0 \end{bmatrix}$$

The following blocks 1230, 1240, 1250 may be performed as part of or in connection with the block 1030 and block 1032 of FIG. 10. Block 1030 involved evaluating whether the measurement plane should be updated based on one or more criteria and block 1032 involved updating the measurement plane such that the measurement plane better matches the control plane. The one or more criteria can be based on, for example, articulations reaching a trigger angle (or within a threshold angle to the trigger angle) or a target angle (or within a threshold angle to the target angle), collecting sufficient articulation history, sufficient time elapsing, or the like.

At block 1230, the process 1200 can involve updating the measurement plane when the computed device articulation crosses a chosen threshold (e.g., a trigger angle, as shown with a second articulation 1232). In some embodiments, a plane of best fit to all articulation history collected may be computed as the updated measurement plane. In some embodiments, some or all of articulation commands provided to the medical instrument 40, resulting articulation, sensed poses, or the like may be compared with the current measurement plane to determine the best fit.

For example, where the articulation command provided were to strictly articulate on the current measurement plane but the resulting articulation detected based on the sensed poses was off the current measurement plane, the current measurement plane may be updated to a plane of best fit to the true articulation of the distal end 442. Updating the measurement plane may provide a more accurate and meaningful measure of the articulation of the device. When the measurement plane is updated, the mismatch between a control plane and a measurement plane may be reduced or eliminated. In some embodiments, the measurement plane may be updated using one or more relationships (e.g., transformation matrices, translations, rotations, etc.). The updating the measurement plane may align the current measurement plane with the control plane or convert coordinates in the current measurement plane to corresponding coordinates in the control plane. Additionally, Code (3) may be executed to update the computed angle and/or the normal vector based on the updated measurement plane.

At block 1240, the process 1200 can involve updating the measurement plane when articulation reaches a first target angle (as shown with a third articulation 1242). Here, the measurement plane may be updated in a similar manner as at block 1230 but with more collected articulation history. Additionally, Code (3) may be executed to update the computed angle and/or the normal vector based on the updated measurement plane. The process of updating the measurement plane once the device has reached a trigger angle can be repeated to further refine the measured measurement plane.

At block 1250, the process 1200 can involve updating the measurement plane when articulation reaches a second target angle (as shown with a fourth articulation 1252). Here, the measurement plane may be updated in a similar manner as at block 1230 and at block 1240 but with even more collected articulation history. The articulation spanning the first pointing vector and the second pointing vector provide substantially greater amount of articulation history and may provide a substantially more accurate measurement plane, as well as a substantially more accurate normal vector. Additionally, Code (3) may be executed to update the computed angle and/or the normal vector based on the updated measurement plane.

At block 1260, the process 1200 can involve determining whether the measurement plane should be locked (e.g., prevented from further updates). In some embodiments, the determination may be based on various thresholds including: (i) an amount of articulation history collected, (ii) an error metric evaluating the mismatch between the measurement plane and the control plane, (iii) a number of measurement plane updates performed, (iv) a set time duration has passed since initialization, or the like. Locking in the measurement plane may allow the medical system 100 to run more efficiently by no longer requiring storage and processing of an increasingly large pool of historical data to use for computing a new measurement plane.

When it is determined that the measurement plane is to be locked, the process 1200 may end at block 1270. Otherwise, the process 1200 may return to any of blocks 1230, 1240, 1250 to continue to update the measurement plane.

Combined Angle Computation Flow Diagram

Various angle methods were described in the present disclosure with their inner workings, limitations, and, in some instances, how those limitations may be addressed. The methods described include the unsigned angle method, the signed angle method, and the projected angle method. In some embodiments, certain disclosures of one computation method may be applied to another computation method. For example, vector projections described in relation to the projected angle method may be applied to unsigned angle method. Furthermore, two or more computation methods may be combined for angle computation. For example, the unsigned angle method may be used to compute articulation angles less than 180 degrees (or some angle threshold) and the projected signed angle method may be used to compute articulation angles greater than 180 degrees (or the angle threshold). The unsigned angle method may also be used when it is not possible to accurately estimate, measure, or otherwise determine a relevant measurement plane in which the angle should be measured.

Figure 13:
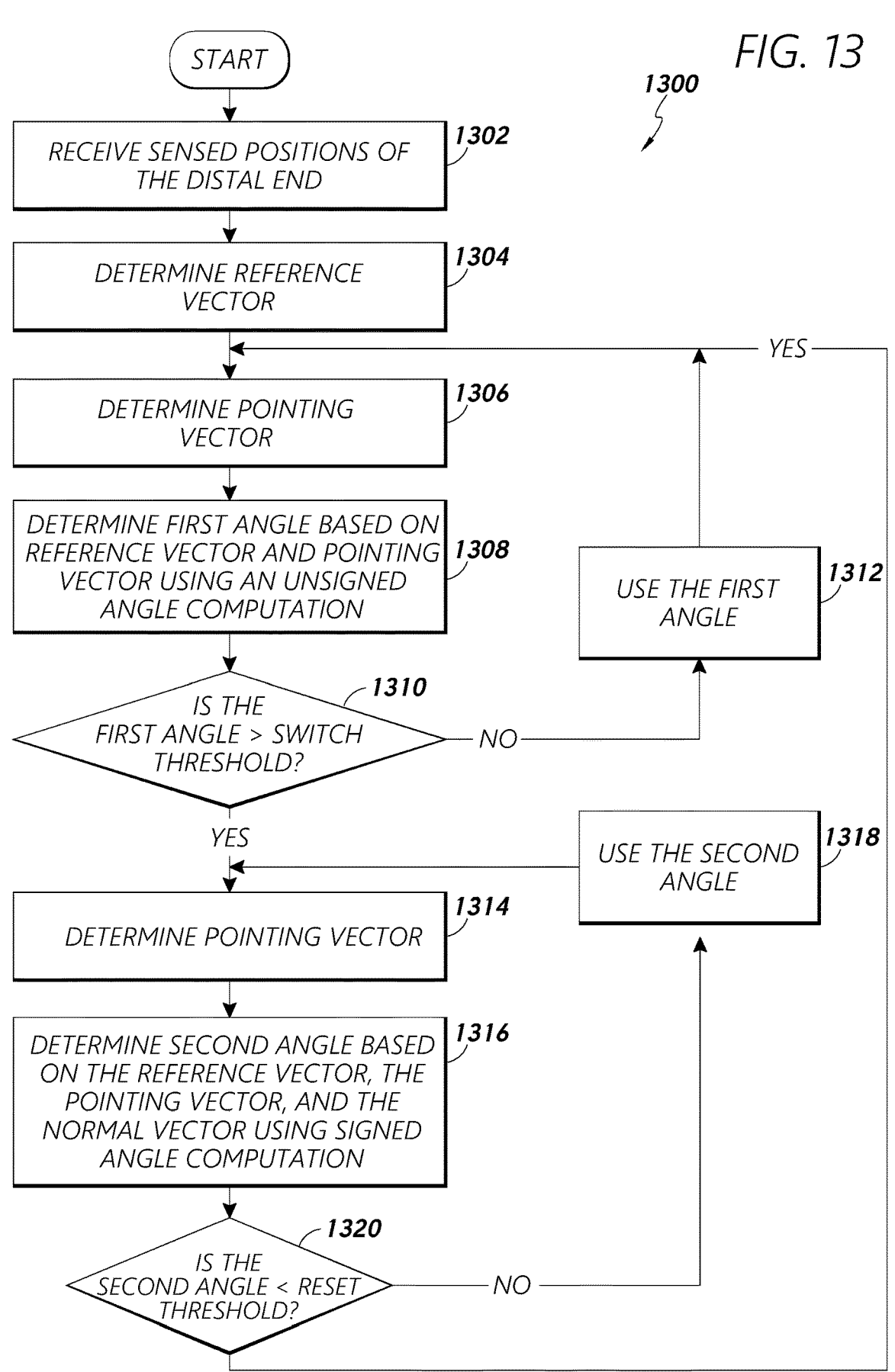
FIG. 13 illustrates a flow diagram of a process for computing an articulation angle with a combined angle method, in accordance with one or more embodiments.

FIG. 13 is a flow diagram of a process 1300 for computing an articulation angle with a combined angle method, in accordance with one or more embodiments. At block 1302, the process 1300 can involve receiving one or more sensed poses of the distal end 442 of the medical instrument flexible elongated body 37. The sensed pose may be one of several sensed poses received as a time sequence, and each may depend on or correspond to how the flexible elongated body 37 is bent. The sensed pose may be produced by any suitable pose tracking subsystem (e.g., a 3D pose tracking subsystem).

At block 1304, the process 1300 can involve determining a reference vector. In one aspect, the reference vector may have been previously determined in a laboratory setting (and stored in memory) for a specimen of the medical instrument 40 that was in its unbent state or in another known state (or equivalently the distal end was in some known pose). Alternatively, or in addition, the reference vector may be determined in-the-field, as pointing to or from an initial sensed pose of the distal end 442. The reference vector can also be updated as needed.

At block 1306, the process 1300 can involve determining a pointing vector from a sample of the sensed pose of the distal end of the flexible elongated body 37. The pointing vector may be defined as pointing along and to a tip of the distal end 442 and may be updated for each sample of the sensed pose of the distal end (once the flexible elongated body 37 starts to bend).

At block 1308, the process 1300 can involve computing a first angle between the pointing vector and the reference vector based on the unsigned angle method of Equation (1). If this first angle is "small enough" then first angle is likely to be accurate. Whether the first angle is "small enough" may be determined based on a comparison to a switch threshold which may be set at any angle at or below 180 degrees (e.g., 180 degrees, 150 degrees, 120 degrees, 90 degrees, etc.).

At block 1310, the process 1300 can involve determining whether the first angle is greater than the switch threshold. When the first angle is not greater than the switch threshold, and as such the first angle is likely to be accurate, the first angle can be used to either characterize or control the medical instrument 40 at block 1312. The process 1300 then loops back to block 1306 to sample the next pointing vector and to continue unsigned angle computations.

Alternatively, when the first angle is indeed greater than the switch threshold, then the process 1300 can proceed to block 1314 since the first angle is more prone to errors as previously described. Additionally, further bending of the flexible elongated body 37 in the same direction likely increases the likelihood that the first angle will no longer be an accurate measure of the desired property of the device. It is noted that, although the conditional logic of block 1310 is described as a greater than condition, the conditional logic may be implemented with other antecedents and consequents (e.g., when the first angle is less than the switch threshold, proceed to block 1312).

At block 1314, the process 1300 can involve determining a pointing vector for a sample of the sensed pose of the distal end of the flexible elongated body 37. When the pointing vector does not need to be updated (e.g., previously determined pointing vector at block 1306 is accurate), then the process 1300 can proceed to block 1316 immediately.

At block 1316, the process 1300 can involve determining a second angle based on the reference vector, pointing vector, and normal vector. This second angle is determined based on the signed angle methods of Equation (2) or (3). Detailed descriptions of the signed angle methods were provided in the process 1000 of FIG. 10 and detailed descriptions of in initializing, guessing, and updating the normal vector were provided in the process 1200 of FIG. 12.

At block 1318, the process 1300 can involve determining whether the second angle is lesser than a reset threshold. The reset threshold may be a threshold at which the medical instrument 40 may switch back to the unsigned angle method. The reset threshold may be the same or smaller than the switch threshold. For example, when the switch threshold is 150 degrees, the reset threshold may be 120 degrees to allow some room of confidence between switching angle computation methods. When the second angle is greater than or equal to the reset threshold, and as such only the signed angle methods may be accurate, the second angle can be used to either characterize or control the medical instrument 40 at block 1320. The process 1300 then loops back to block 1314 to sample the next pointing vector and to continue signed angle computations.

Alternatively, when the second angle is indeed less than the switch threshold, then the process 1300 can proceed to block 1306 to use the more efficient unsigned angle method. In other words, the process 1300 discontinues the large/signed angle computation at that point but reverts back to using the unsigned angle method at block 1306.

It is noted that, although the conditional logic of block 1318 is described as a less than condition, the conditional logic may be implemented with other antecedents and consequents (e.g., when the second angle is greater than the reset threshold, proceed to block 1320).

At block 1312 and block 1320, the computed angle (e.g., the first angle or the second angle) may be used to characterize or control the flexible elongated flexible body 37. The characterization or the control may involve associating the computed angle with an existing command that resulted in the current bent state of the flexible elongated flexible body 37. Note here this may include unwrapping the angle into a positive articulation amount (by adding 360 to the angle).

In some embodiments, a number of computed angles, which are associated with a range of bent states of the flexible elongated flexible body 37, can populate a look up table that can be stored and then used subsequently, for example to perform open loop control of the same medical instrument 40 or another specimen of it (that has the same design for the flexible elongated body 37).

In some embodiments, the medical system 100 may generate a new command for bending or articulating the flexible elongated body 37, using the computed angle. The new command may be generated in an open loop manner, e.g., based on a previously stored look up table, or it may be generated in a closed loop manner which uses the computed angle as feedback.

If greater accuracy is desired, for example to use the angle for closed loop control of the medical instrument 40, then the plane and the normal vector may be updated based on the process 1200 of FIG. 12.

The processes 1000, 1200, 1300 of FIGS. 10, 12, and 13, respectively, may be performed by a digital processor which may, for example, be part of the control circuitry 251 of the control system 50, in the medical system 100 described above. The processor may be configured or programmed by instructions stored in a machine-readable medium, such as solid-state memory, to perform the following operations. Note that the operations depicted in the diagram or those described below can take place in an order that is different than in the sequence they are shown in the diagram or described below, and some may take place simultaneously or concurrently.

While certain aspects have been described above and shown in the accompanying drawings, it is to be understood that such are merely illustrative of and not restrictive on the invention, as the invention is not limited to the specific constructions and arrangements shown and described. Various modifications may occur to those of ordinary skill in the art. The description is thus to be regarded as illustrative instead of limiting.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for case of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A method for controlling or characterizing a medical instrument, the method comprising:
   receiving at least one sensed pose of a distal end of a flexible elongated body;
   determining a reference vector;
   determining a pointing vector based on the at least one sensed pose;
   projecting the pointing vector onto a measurement plane;
   determining an articulation angle based on the projected pointing vector, the reference vector, and a normal vector associated with the measurement plane; and
   generating a command for controlling the flexible elongated body based on the articulation angle.

2. The method of claim 1, further comprising:
   projecting the reference vector onto the measurement plane.

3. The method of claim 1, wherein the determining the articulation angle comprises:
   applying an inverse trigonometric function.

4. The method of claim 3, wherein the inverse trigonometric function is an inverse tangent function.

5. The method of claim 4, wherein the inverse tangent function has an output range of 360 degrees.

6. The method of claim 1, wherein the normal vector represents a clockwise articulation or a counterclockwise articulation on the normal vector.

7. The method of claim 1, wherein the determining the articulation angle comprises:
   determining a cross product based on the reference vector and the pointing vector.

8. The method of claim 7, wherein the determining the articulation angle comprises:
   determining an inner product of the cross product and the normal vector.

9. The method of claim 1, wherein the determining the articulation angle comprises:
   determining that the articulation angle is negative; and
   based on the determination that the articulation angle is negative, adding 360 degrees to the articulation angle.

10. The method of claim 1, wherein the determining the articulation angle comprises:
   determining that a magnitude of the articulation angle is greater than a wraparound threshold; and
   based on the determination that the magnitude of the articulation angle is greater than the wraparound threshold, adding 360 degrees to the articulation angle.

11. The method of claim 1, wherein the determining the articulation angle comprises:
   determining that the articulation angle is negative; and
   based on the determination that the articulation angle is negative, reversing a direction of the normal vector.

12. The method of claim 1, wherein the determining the articulation angle comprises:
   determining that the articulation angle is negative; and
   based on the determination that the articulation angle is negative, changing a sign of the articulation angle to positive.

13. The method of claim 1, wherein the pointing vector is of an initial articulation, the method further comprising:
   determining that the articulation angle is negative; and
   based on the determination that the articulation angle is negative:
      changing a sign of the articulation angle to positive; and
      reversing a direction of the normal vector.

14. The method of claim 1, further comprising:
   accumulating articulation history of the flexible elongated body, wherein the articulation history comprises a time sequence of one or more pointing vectors;
   determining a plane of best fit for the articulation history; and
   updating the measurement plane with the plane of best fit.

15. The method of claim 14, wherein the updating the measurement plane is in response to a determination that the articulation angle has reached a target angle.

16. The method of claim 14, wherein the updating the measurement plane comprises:
   applying a transformation matrix to the measurement plane.

17. The method of claim 14, further comprising:
   determining that an amount of the articulation history is greater than a threshold amount; and
   based on the determination that the amount of the articulation history is greater than the threshold amount, preventing the measurement plane from further updates.

18. The method of claim 1, wherein the determining the articulation angle comprises:
   determining that the articulation angle is less than a threshold; and based on the determination that the articulation angle is less than the threshold, determining the articulation angle based on the pointing vector and the reference vector using an inverse cosine function.

19. A system, comprising:

control circuitry configured to communicatively couple to a flexible elongated body of a medical instrument;

wherein the control circuitry is configured to:

receive at least one sensed pose of a distal end of the flexible elongated body;

determine a reference vector;

determine a pointing vector based on the at least one sensed pose;

project the pointing vector onto a measurement plane;

determine an articulation angle based on the projected pointing vector, the reference vector, and a normal vector associated with the measurement plane; and generate a command for controlling the flexible elongated body based on the articulation angle.

20. A non-transient computer readable medium containing program instructions for causing a computer to perform a method of:

receiving at least one sensed pose of a distal end of a flexible elongated body of a medical instrument;

determining a reference vector;

determining a pointing vector based on the at least one sensed pose;

projecting the pointing vector onto a measurement plane;

determining an articulation angle based on the projected pointing vector, the reference vector, and a normal vector associated with the measurement plane; and generating a command for controlling the flexible elongated body based on the articulation angle.

* * * * *